US007951614B2

(12) United States Patent (10) Patent No.: US 7,951,614 B2
Tamarkin et al. (45) Date of Patent: May 31, 2011

(54) METHODS AND COMPOSITIONS FOR THE PRODUCTION OF MONOCLONAL ANTIBODIES

(75) Inventors: Lawrence Tamarkin, Rockville, MD (US); Giulio F. Paciotti, Baltimore, MD (US)

(73) Assignee: CytImmune Sciences, Inc., Rockville, MD (US)

(*) Notice: Subject to any disclaimer, the term of this patent is extended or adjusted under 35 U.S.C. 154(b) by 0 days.

(21) Appl. No.: 12/549,207

(22) Filed: Aug. 27, 2009

(65) Prior Publication Data

US 2010/0068261 A1   Mar. 18, 2010

Related U.S. Application Data

(62) Division of application No. 11/004,623, filed on Dec. 2, 2004, now abandoned.

(60) Provisional application No. 60/526,360, filed on Dec. 2, 2003.

(51) Int. Cl.
*G01N 33/553* (2006.01)
*A61K 45/00* (2006.01)
*A61K 47/00* (2006.01)

(52) U.S. Cl. ............... 436/525; 424/278.1; 530/811

(58) Field of Classification Search .................. None
See application file for complete search history.

(56) References Cited

U.S. PATENT DOCUMENTS

| | | | |
|---|---|---|---|
| 2,768,958 A | 10/1956 | Stewart et al. |
| 2,785,153 A | 3/1957 | Locke et al. |
| 3,145,144 A | 8/1964 | Ando et al. |
| 3,149,036 A | 9/1964 | Woodhour et al. |
| 3,269,912 A | 8/1966 | Grafe |
| 3,399,263 A | 8/1968 | Strazdins et al. |
| 3,531,565 A | 9/1970 | Webb et al. |
| 3,577,523 A | 5/1971 | Stolar et al. |
| 3,651,211 A | 3/1972 | Gillchriest et al. |
| 3,819,820 A | 6/1974 | Lorina et al. |
| 3,919,413 A | 11/1975 | Mebus |
| 3,983,228 A | 9/1976 | Woodhour et al. |
| 4,016,252 A | 4/1977 | Relyveld |
| 4,053,587 A | 10/1977 | Davidson et al. |
| 4,069,313 A | 1/1978 | Woodhour et al. |
| 4,177,263 A | 12/1979 | Rosenberg et al. |
| 4,196,185 A | 4/1980 | Focella et al. |
| 4,197,237 A | 4/1980 | Leute et al. |
| 4,197,286 A | 4/1980 | Rao |
| 4,213,964 A | 7/1980 | Buckler |
| 4,215,036 A | 7/1980 | Malley |
| 4,218,436 A | 8/1980 | Fitzpatrick |
| 4,329,281 A | 5/1982 | Christenson et al. |
| 4,330,530 A | 5/1982 | Baker |
| 4,332,787 A | 6/1982 | Homcy et al. |
| 4,339,437 A | 7/1982 | Rosenberg et al. |
| 4,346,074 A | 8/1982 | Gilmour et al. |
| 4,451,570 A | 5/1984 | Royston et al. |
| 4,487,780 A | 12/1984 | Scheinberg |
| 4,578,270 A | 3/1986 | Csizer et al. |
| 4,594,325 A | 6/1986 | Lundak |
| 4,608,252 A | 8/1986 | Khanna et al. |
| 4,624,921 A | 11/1986 | Larrick et al. |
| 4,624,923 A | 11/1986 | Margel |
| 4,639,336 A | 1/1987 | Jouquey et al. |
| 4,657,763 A | 4/1987 | Finkelstein |
| 4,693,975 A | 9/1987 | Kozbor et al. |
| 4,710,378 A | 12/1987 | Ohtomo et al. |
| 4,720,459 A | 1/1988 | Winkelhake |
| 4,740,589 A | 4/1988 | Moreno |
| 4,744,760 A | 5/1988 | Molday |
| 4,753,873 A | 6/1988 | Beltz et al. |
| 4,812,556 A | 3/1989 | Vahlne et al. |
| 4,880,750 A | 11/1989 | Francoeur |
| 4,882,423 A | 11/1989 | Taguchi et al. |
| 4,906,564 A | 3/1990 | Lyon et al. |
| 4,977,286 A | 12/1990 | Nicolaou et al. |
| 5,017,687 A | 5/1991 | Vahlne et al. |
| 5,019,497 A | 5/1991 | Olsson |
| 5,035,995 A | 7/1991 | Taguchi et al. |
| 5,047,523 A | 9/1991 | Woods et al. |
| 5,112,606 A | 5/1992 | Shiosaka et al. |
| 5,126,253 A | 6/1992 | Nakanishi et al. |
| 5,169,754 A | 12/1992 | Siiman et al. |
| 5,242,828 A | 9/1993 | Bergstrom et al. |
| 5,248,772 A | 9/1993 | Siiman et al. |
| 5,264,221 A | 11/1993 | Tagawa et al. |
| 5,294,369 A | 3/1994 | Shigekawa et al. |
| 5,376,556 A | 12/1994 | Tarcha et al. |
| 5,384,073 A | 1/1995 | Shigekawa et al. |
| 5,434,088 A | 7/1995 | Ikeda et al. |
| 5,436,161 A | 7/1995 | Bergstrom et al. |
| 5,446,090 A | 8/1995 | Harris |
| 5,466,609 A | 11/1995 | Siiman et al. |
| 5,498,421 A | 3/1996 | Grinstaff et al. |
| 5,521,289 A | 5/1996 | Hainfeld et al. |
| 5,639,725 A | 6/1997 | O'Reilly et al. |
| 5,686,578 A | 11/1997 | Goldenberg |
| 5,736,410 A | 4/1998 | Zarling et al. |
| 5,874,226 A | 2/1999 | Zeytinoglu et al. |
| 5,972,720 A | 10/1999 | Nichtl et al. |
| 6,274,552 B1 | 8/2001 | Tamarkin et al. |
| 6,407,218 B1 | 6/2002 | Tamarkin et al. |

(Continued)

FOREIGN PATENT DOCUMENTS

AU   760035   8/2003

(Continued)

OTHER PUBLICATIONS

Dynabeads product information, 2010, pp. 1-3.*

(Continued)

*Primary Examiner* — Amy E Juedes
(74) *Attorney, Agent, or Firm* — Johnson & Associates

(57) ABSTRACT

The present invention comprises compositions and methods for making monoclonal antibodies. The present invention further comprises vectors that replicate the immune system components, particularly an antigen-presenting cell (APC) element of the immune synapse. Additionally, the present invention may further comprise synthetic T-cells.

15 Claims, 14 Drawing Sheets

U.S. PATENT DOCUMENTS

| | | |
|---|---|---|
| 6,447,765 B1 | 9/2002 | Horwitz |
| 6,528,051 B2 | 3/2003 | Tamarkin et al. |
| 6,528,485 B1 | 3/2003 | Veronese et al. |
| 6,530,944 B2 | 3/2003 | West et al. |
| 6,593,292 B1 | 7/2003 | Rothbard et al. |
| 6,624,886 B2 | 9/2003 | Natan et al. |
| 6,734,168 B2 | 5/2004 | Stern et al. |
| 6,821,529 B2 | 11/2004 | Nelson |
| 6,869,932 B2 | 3/2005 | Veronese et al. |
| 7,229,841 B2 | 6/2007 | Tamarkin et al. |
| 7,387,900 B2 | 6/2008 | Tamarkin et al. |
| 7,547,438 B2 | 6/2009 | Thomas et al. |
| 2001/0055581 A1 | 12/2001 | Tamarkin et al. |
| 2002/0071826 A1 | 6/2002 | Tamarkin et al. |
| 2003/0053983 A1 | 3/2003 | Tamarkin et al. |
| 2003/0180252 A1 | 9/2003 | Tamarkin et al. |
| 2003/0235908 A1* | 12/2003 | Berenson et al. ............ 435/372 |
| 2004/0018203 A1 | 1/2004 | Pastan et al. |
| 2004/0029794 A1 | 2/2004 | Veronese et al. |
| 2004/0054139 A1 | 3/2004 | Page et al. |
| 2004/0204576 A1 | 10/2004 | Jackson et al. |
| 2004/0213760 A1 | 10/2004 | Tamarkin et al. |
| 2005/0003431 A1 | 1/2005 | Wucherpfennig et al. |
| 2005/0085513 A1 | 4/2005 | Baloglu et al. |
| 2007/0014798 A1 | 1/2007 | Rieber |
| 2007/0160572 A1 | 7/2007 | Tamarkin et al. |
| 2007/0231408 A1 | 10/2007 | Tamarkin et al. |

FOREIGN PATENT DOCUMENTS

| | | |
|---|---|---|
| AU | 757357 | 3/2004 |
| AU | 2003231660 B2 | 8/2006 |
| AU | 2003204353 | 11/2006 |
| CA | 2158475 | 3/1994 |
| EP | 0 044 722 | 1/1982 |
| EP | 0 156 242 | 12/1985 |
| EP | 0 179 483 | 4/1986 |
| EP | 0 269 408 | 6/1988 |
| EP | 0 441 120 A2 | 8/1991 |
| EP | 0 489 465 A2 | 6/1992 |
| EP | 0 667 398 A2 | 8/1995 |
| EP | 0 811 846 B1 | 12/1997 |
| EP | 0 486 526 B2 | 3/2001 |
| EP | 1 401 376 | 3/2004 |
| EP | 0 690 722 B1 | 6/2004 |
| EP | 1 039 933 B1 | 2/2006 |
| EP | 1 044 022 B1 | 3/2006 |
| FR | 2 334 366 | 7/1977 |
| FR | 2 533 827 | 4/1984 |
| GB | 981242 | 1/1965 |
| JP | 05-017369 | 1/1993 |
| JP | 6-118083 | 4/1994 |
| WO | WO 90/05303 A1 | 5/1990 |
| WO | WO 91/02078 A1 | 2/1991 |
| WO | WO 91/15242 A1 | 10/1991 |
| WO | WO 93/15117 | 8/1993 |
| WO | WO 93/21528 A1 | 10/1993 |
| WO | WO 94/21240 A2 | 9/1994 |
| WO | WO 94/21288 | 9/1994 |
| WO | WO 95/24918 A1 | 9/1995 |
| WO | WO 96/04313 | 2/1996 |
| WO | WO 97/29131 A1 | 8/1997 |
| WO | WO 99/24066 | 5/1999 |
| WO | WO 99/24077 A2 | 5/1999 |
| WO | WO 02/087509 A2 | 11/2002 |

OTHER PUBLICATIONS

Li et al., 2000, Colloids and surfaces, vol. 175: 217-223.*

FDA Updates, *FDA Consumer*, vol./Iss: 33 (6), pp. 5, Nov. 1, 1999.

PCT International Search Report cited in PCT/US04/40785, *PCT International Search Report*, pp. 1-2, Oct. 25, 2005.

PCT International Search Report cited in PCT/US08/82984, *PCT International Search Report*, pp. 1-4, Feb. 3, 2009.

Balkwill et al., The Cytokine Network, *Immunology Today*, vol./Iss: 10(9), pp. 299-304, Jan. 1, 1989.

Borrebaeck et al., Human Monoclonal Antibodies Produced by Primary in Vitro Immunization of Peripheral Blood Lymphocytes, *Proceedings of the National Academy of Science USA*, vol./Iss: 85, pp. 3995-3999, Jun. 1, 1986.

Brust et al., Novel Gold-Dithiol Nano-Networks with Non-Metallic Electronic Properties, *Advanced Materials*, vol./Iss: 7 (9), pp. 795-797, Jan. 1, 1995.

Ciesiolka et al., An 8- to 10-fold Enhancement in Sensitivity for Quantitation of Proteins by Modified Application of Colloidal Gold, *Analytical Biochemistry*, vol./Iss: 168 (2) pp. 280-283, Feb. 1, 1988.

Coulombe et al., Cytochemical Demonstration of Increased Phospholipid Content in Cell Membranes in Chlorphentermine-Induced Phospholipidosis, *Journal of Histochemistry and Cytochemistry*, vol./Iss: 37 (2), pp. 139-147, Jan. 1, 1989.

De Brabander et al., Probing Microtubule-Dependent Intracellular Motility with Nanometer Particle Video Ultramicroscopy (nanovid ultramicroscopy) (Abstract Only), *Cytobios*, vol./Iss: 43, pp. 273-283, Jan. 1, 1985.

Deng et al., Self-Assembled Monolayers of Alkanethiolates Presenting Tri(propylene sulfoxide) Groups Resist the Adsorption of Protein, *Journal of the American Chemical Society*, vol./Iss: 118 (19), pp. 5136-5137, May 15, 1996.

Dominguez et al., Effect of Heart Treatment on the Antigen-Binding Activity of Anti-Peroxidase Immunoglobulins in Bovine Colostrum, *Journal of Dairy Science*, vol./Iss: 80 (12), pp. 3182-3187, Dec. 1, 1998.

Elliott et al., Analysis of Colloidal Gold Probes by Isoelectric Focusing in Agarose Gels, *Analytical Biochemistry*, vol./Iss: 186 (1), pp. 53-59, Apr. 1, 1990.

EPO Searching Authority, Search Report EPO—Application No. 02729092.3, *EPO Search Report*, pp. 1-6, Jul. 13, 2009.

Fraker et al., Passive Immunization Against Tumor Necrosis Factor Partially Abrogates Interleukin 2 Toxicity, *The Journal of Experimental Medicine*, vol./Iss: 170, pp. 1015-1020, Jan. 1, 1989.

Goldstein et al., Cardiovascular Effects of Platelet-Activating Factor, *Lipids*, vol./Iss: 26(212), pp. 1250-1256, Jan. 1, 1991.

Grainger et al, Polymeric Monolayers on Solid Substrates by Spontaneous Adsorption from Solution, *American Chemical Society—Abstracts of Papers*, vol./Iss: Part 1, pp. Paragraph 074, Aug. 20, 1995.

Gref et al., The Controlled Intravenous Delivery of Drugs using PEG-Coated Sterically Stabilized Nanospheres, *Advanced Drug Delivery Reviews*, vol./Iss: 16, pp. 215-233, Jan. 1, 1995.

Hashimoto et al., Action Site of Circulating Interleukin-1 on the Rabbit Brain, *Brain Research*, vol./Iss: 540, pp. 217-223, Jan. 1, 1991.

Hisamatsu et al., Platelet Activating Factor Induced Respiratory Mucosal Damage, *Lipids*, vol./Iss: 26 (12), pp. 1287-1291, Jan. 1, 1991.

Hopkins et al., Early Events Following the Binding of Epidermal Growth Factor to Surface Receptors on Ovarian Granulosa Cells, *European Journal of Cell Biology*, vol./Iss: 24, pp. 259-264, Jan. 1, 1981.

Ito et al., Antitumor Reactivity of Anti-CD3/Anti-CD28 Bead-Activated Lymphoid Cells: Implications for Cell Therapy in a Murine Model, *Journal of Immunotherapy*, vol./Iss: 26 (3), pp. 222-233, Jan. 1, 2003.

Kang et al., Ultrastructural and Immunocytochemical Study of the Uptake and Distribution of Bacterial Lipopolysaccaride in Human Monocytes, *Journal of Leukemia Biology*, vol./Iss: 48, pp. 316-332, Jan. 1, 1990.

Kimball, Chapter 7—B Lymphocytes, *Introduction to Immunology*, pp. 184-190, Jan. 1, 1990.

Kirchner et al., The Development of Neutralizing Antibodies in a Patient Receiving Subcutaneous Recombinant and Natural Interleukin-2, *Cancer*, vol./Iss: 67 (7), pp. 1862-1864, Apr. 1, 1991.

Koganty, R.R., Vaccine Safety: A Case for Synthetic Vaccine Formulations, *Expert Review of Vaccines*, vol./Iss: 2 (6), pp. 725-727, Dec. 1, 2003.

Koning, et al., Selective Transfer of a Lipophilic Prodrug of 5-Fluorodeoxyuridine from Immunoliposomes to Colon Cancer Cells, *Biochimica et Biphysica Acta*, vol./Iss: 1420, pp. 153-167, Jun. 2, 1999.

Lang et al., A New Class of Thiolipids for the Attachment of Lipid Bilayers on Gold Surfaces, *Langmuir*, vol./Iss: 10 (1), pp. 197-210, Jan. 1, 1994.
Lanzavecchia, Identifying Strategies for Immune Interventor, *Science*, vol./Iss: 260, pp. 937-944, Jan. 1, 1993.
Lemmon et al., Preparation and Characterization of Nanocomposites of Poly(ethylene oxide) with Layered Solids, *New Techniques and Approaches,* vol./Iss: Chapter 5, pp. 43-54, Jan. 1, 1995.
Leuvering et al., A Sol Particle Agglutination Assay for Human Chorionic Gonadotrophin, *Journal of Immunological Methods*, vol./Iss: 45 (2), pp. 183-194, Jan. 1, 1981.
Lezzi et al., Chelating Resins Supporting Dithiocarbamate and Methylthiourea Groups in Adsorption of Heavy Metal Ions, *Journal of Applied Polymer Science*, vol./Iss: 54 (7), pp. 889-897, Nov. 14, 1994.
Lezzi et al., Synthesis of Thiol Chelating Resins and Their Adsorption Properties toward Heavy Metal Ions, *Journal of Polymer Science*, vol./Iss: 32, pp. 1877-1883, Jan. 1, 1994.
Li et al., Plasma Protein Interactions with Copolymer-Stabilized Colloids, *Dissertation Abstracts International*, vol./Iss: 54 (7), pp. 3735-B, Jan. 1, 1994.
Mathias et al., Sulfur-Substituted Polyoxyethylenes Sequential Ether-Thioether Copolymers, *Crown Ethers and Phase Transfer Catalysis in Polymer Science*, pp. 359-370, Jan. 1, 1984.
Morris et al., Validation of the Biotinyl Ligand-Avidin-Gold Technique, *Cytochemistry*, vol./Iss: 40, pp. 711-721, Jan. 1, 1992.
Mrksich et al., Surface Plasmon Resonance Permits in Situ Measurement of Protein Adsorption on Self-Assembled Monolayers of Alkanethiolates on Gold, *Langmuir*, vol./Iss: 11, pp. 4383-4385, Jan. 1, 1995.
Nakashima et al., Electrochemical Characterization of an Assembled Monolayer of $\alpha$-Methoxy-$\omega$-mercapto-poly(ethylene glycol) on Gold and Complex Formation of the Monolayer with $\alpha$-Cyclodextrin, *Chemistry Letters*, pp. 731-732, Jan. 1, 1996.
Niwa et al., Two-Dimensional Array of Poly(methacrylic acid) Brushes on Gold Substrates. Interaction with Ferrocen-Terminated Poly(oxyethylene)s, *Macromolecules*, vol./Iss: 28 (23), pp. 7770-7774, Nov. 6, 1995.
Ohmann et al., Expression of Tumor Necrosis Factor-$\alpha$ Receptors on Bovine Macrophges. Lymphocytes and Polymorphonuclear Luekocytes, Internalization of Receptor-Bound Ligand, and Some Functional Effects, *Lymphokine Research*, vol./Iss: 9 (1), pp. 43-58, Jan. 1, 1990.
Otsuka et al., Quantitative and Reversible Lectin-Induced Association of Gold Nanoparticles Modified with $\alpha$-Lactosyl-$\omega$-mercapto-poly(ethylene glycol), *Journal of the American Chemical Society*, vol./Iss: 123, pp. 8226-8230, Feb. 20, 2001.
Paciotti et al., Interleukin 2 Differentially Effects the Proliferation of a Hormone-Dependent and a Hormone-Independent Human Breast Cancer Cell Line in Vitro and in Vivo, *Anti-Cancer Research*, vol./Iss: 8, pp. 1233-1240, Jan. 1, 1988.
Paciotti et al., Interleukin 1$\alpha$ Differentially Synchronizes Estrogen Dependent and Estrogen-Independent Human Breast Cells in $G_0/G_1$ Phase of the Cell Cycle, *Anti-Cancer Research*, vol./Iss: 11, pp. 25-32, Jan. 1, 1991.
Paciotti et al., Interleukin 1 Directly Regulates Hormone-Dependent Human Breast Cancer Cell Proliferation in Vitro, *Molecular Endocrinology*, vol./Iss: 2, pp. 459-464, Jan. 1, 1988.
Paciotti et al., (XP-001537146) #3858—Comparison of the Toxicity and Pharmacokinetics of Neat and Colloidal Gold Boung TNF, *Proceedings of the American Association for Cancer Research*, vol./Iss: 40, pp. 585, Mar. 1, 1999.
Paciotti et al., (XP-001537149) #1048—The Use of Colloidal Gold in Cytokine Immununotherapy, *Proceedings of the American Association for Cancer Research*, vol./Iss: 39, pp. 153, Mar. 1, 1998.
Peters et al., Binding and Internalization of Biotinylated Interleukin-2 in Human Lymphocytes, *Blood*, vol./Iss: 76, pp. 97-104, Jan. 1, 1990.
Prakken et al., Artificial Antigen-Presenting Cells as a Tool to Exploit the Immune 'Synapse', *Nature Medicine*, vol./Iss: 6 (12), pp. 1406-1410, Dec. 1, 2000.
Prime et al., Adsorption of Proteins onto Surfaces Containing End-Attached Oligo(ethylene oxide): A Model System Using Self-Assembled Monolayers, *Journal of the American Chemical Society*, vol./Iss: 115, pp. 10714-10721, Jan. 1, 1993.
Rabolt, J.F., Design and Construction of Two Component Heterogenous Polymer Surfaces by Self Assembly, *Polymer Preprints*, vol./Iss: 36 (1), pp. 84, Apr. 1, 1995.
Roitt et al., The Cytokine Network, *Immunology*, vol./Iss: 3rd ed., pp. 8-15, Jan. 1, 1993.
Stolnik et al., The Effects of Surface Coverage and Conformation of Poly(ethylene oxide) (PEO) Chains of Poloxamer 407 on the Biological Fate of Model Colloidal Drug Carriers, *Biochimica et Biphysica Acta*, vol./Iss: 1514, pp. 261-279, Oct. 1, 2001.
Thompson et al., A Phase I Trial of CD3/CD28-Activated T Cells (Xcellerated T Cells) and Interleukin-2 in Patients with Metastatic Renal Cell Carcinoma, *Clinical Cancer Research*, vol./Iss: 9, pp. 3562-3570, Sep. 1, 2003.
Tomii et al., Production of Anti-Platelet-Activating Factor Antibodies by the Use of Colloidal Gold as Carrier, *Japanes Journal of Medical Science and Biology*, vol./Iss: 44, pp. 75-80, Jan. 1, 1991.
USPTO Office Action—cited in U.S. Appl. No. 11/046,204, *USPTO Office Action*, pp. 1-20, Oct. 16, 2008.
Van Rensen et al., Liposomes with Incorporated MHC Class II/Peptide Complexes as Antigen Presenting Vesicles for Specific T Cell Activation, *Pharmaceutical Research*, vol./Iss: 16 (2), pp. 198-204, Jan. 1, 1999.
Vidal et al., Steric Stabilization of Polystyrene Colloids Using Thiol-ended Polyethylene Oxide, *Polymers for Advanced Technologies*, vol./Iss: 6, pp. 473-479, Nov. 15, 1994.
Walden et al., Induction of Regulatory T-lymphocyte Responses by Liposomes Carrying Major Histocompatibility Complex Molecules and Foreign Antigen, *Nature*, vol./Iss: 315, pp. 327-329, May 23, 1985.
Calabresi et al., Chemotherapy of Neoplastic Diseases, *Goodman & Gilman's The Pharmacological Basis of Therapeutics*, vol./Iss: 9th Edition, pp. 1225-1232, Jan. 1, 1996.
EPO Search Report, EPO Application 04821049.6 Search Report, *EPO Search Report*, pp. 1-10, Oct. 19, 2009.
Gallego et al., Ultrastructural Identification of the Splenic Follicular Dendritic Cells in the Chicken, *The Anatomical Record*, vol./Iss: 242, pp. 220-224, Jan. 1, 1995.
Japanese Patent Office, Japanese Patent Application 2000-520153 Office Action as translated by Foreign Associate, *Japanese Office Action*, pp. 1-10, Oct. 6, 2009.
Japanese Publication, Japanese Laid-Open Publication No. 9-107980 English Abstract only—of Japanese Patent Application 08-231415, pp. 1-3, Apr. 28, 1997.
Magez et al., Specific Uptake of Tumor Necrosis Factor-a is Involved in Growth Control of *Trypanosoma brucei, The Journal of Cell Biology*, vol./Iss: 137 (3), pp. 715-727, May 5, 1997.
USPTO Office Action—cited in U.S. Appl. No. 11/516,175, *USPTO Office Action*, pp. 1-9, Jun. 5, 2009.
Office Action—Peoples Republic of China—Application No. 200480041234.5, *Peoples Republic of China—Office Action*, pp. 1-18, Jun. 27, 2008.
Australian Office Action—Application No. 2004311630, *Australian Office Action*, pp. 1-4, Oct. 9, 2009.
Japanese Office Action cited in 2000-520162 (with English translation), *Japanese Office Action*, pp. 1-3, Jun. 4, 2010.
Japanese Office Action cited in 2000-520162 (with English translation), *Japanese Office Action*, pp. 1-3, Oct. 22, 2009.
Japanese Office Action cited in 2000-520162 (with English translation), *Japanese Office Action*, pp. 1-7, Apr. 14, 2009.
EPO Search Report—98957757.2, *EPO Search Report*, pp. 1-4, Aug. 2, 2004.
EPO Search Report—98957757.2, *EPO Search Report*, pp. 1-3, Oct. 31, 2003.
Canadian Office Action—2,309,604, *Canadian Office Action*, pp. 1-2, Feb. 11, 2008.
Canadian Office Action—2,309,604, *Canadian Office Action*, pp. 1-4, May 18, 2006.
USPTO Office Action—cited in U.S. Appl. No. 10/672,144, *USPTO Office Action*, pp. 1-10, Apr. 15, 2009.
USPTO Office Action—cited in U.S. Appl. No. 10/672,144, *USPTO Office Action*, pp. 1-8, Jan. 20, 2010.

USPTO Office Action cited in U.S. Appl. No. 10/672,144, *U.S. PTO Office Action*, pp. 1-5, Nov. 15, 2010.

USPTO Office Action—cited in U.S. Appl. No. 10/672,144, *USPTO Office Action*, pp. 108, Oct. 17, 2007.

USPTO Office Action—cited in U.S. Appl. No. 10/672,144, *USPTO Office Action*, pp. 1-6, Aug. 5, 2010.

Baron, S., Figure: Genetic Map of Adenovirus Type 2, *Medical Microbiology*, vol./Iss: 4th Ed., pp. Fig. 67-3, Jan. 1, 1996.

Calabresi et al., Chemotherapy of Neoplastic Diseases, *Goodman & Gilman's The Pharmacological Basis of Therapeutics*, vol./Iss: 9th Edition, pp. 1260-1261, 1293, Jan. 1, 1996.

De Roe et al., A Model of Protein—Colloidal Gold Interactions, *The Journal of Histochemistry and Cytochemistry*, vol./Iss: 35 (11), pp. 1191-1198, Jan. 1, 1987.

EPO Search Report, EPO Application 04821049.6 Search Report, *EPO Search Report*, pp. 1-10, Oct. 19, 2009.

Fitzgerald et al., Adenovirus-Induced Release of Epidermal Growth Factor and *Pseudomonas* Toxin into the Cytosol of KB Cells during Receptor-Mediated Endocytosis, *Cell*, vol./Iss: 32, pp. 607-617, Feb. 1, 1983.

USPTO Office Action—cited in U.S. Appl. No. 12/267,847, *USPTO Office Action*, pp. 1-11, Mar. 18, 2010.

U.S. PTO Office Action cited in U.S. Appl. No. 12/267,847, *U.S. PTO Office Action*, pp. 1-11, Oct. 5, 2010.

USPTO Office Action—U.S. Appl. No. 11/004,623, *USPTO Office Action*, pp. 1-12, Aug. 5, 2008.

USPTO Office Action—U.S. Appl. No. 11/004,623, *USPTO Office Action*, pp. 1-16, Nov. 6, 2007.

USPTO Office Action—U.S. Appl. No. 11/004,623, *USPTO Office Action*, pp. 1-22, Feb. 22, 2007.

USPTO Office Action—cite in U.S. Appl. No. 09/189,657, *USPTO Office Action*, pp. 1-15, Apr. 11, 2008.

USPTO Office Action—cited in U.S. Appl. No. 12/250,126, *USPTO Office Action*, pp. 1-12, Jun. 7, 2010.

Van Den Pol, A. N., Colloidal Gold and Biotin-Avidin Conjugates as Ultrastructural Markers for Neural Antigens, *Quarterly Journal of Experimental Physiology*, vol. 69, pp. 1-33, Jan. 1, 1984.

\* cited by examiner

METHODS AND COMPOSITIONS FOR THE PRODUCTION OF MONOCLONAL ANTIBODIES

CROSS-REFERENCE TO RELATED APPLICATIONS

This application is a divisional of U.S. patent application Ser. No. 11/004,623 filed Dec. 2, 2004 now abandoned which claims priority to U.S. Provisional Application No. 60/526,360 filed Dec. 2, 2003.

FIELD OF THE INVENTION

The present invention relates generally to immunology. The present invention further relates to methods and compositions for the production of monoclonal antibodies and in vitro methods for production of such antibodies.

BACKGROUND OF THE INVENTION

The introduction of desired agents into specific target cells has been a challenge to scientists for a long time. The challenge of specific targeting of agents is to get an adequate amount of the agent or the correct agent to the target cells of an organism without providing too much exposure of the rest of the organism. A very desired target for delivery of specific agents is the immune system. The immune system is a complex response system of the body that involves many different kinds of cells that have differing activities. Activation of one portion of the immune system usually causes a variety of responses due to unwanted activation of other related portions of the system. Currently, there are no satisfactory methods or compositions for producing a specifically desired response by targeting the specific components of the immune system.

The immune system is a complex interactive system of the body that involves a wide variety of components, including cells, and cellular factors, which interact with stimuli from both inside the body and outside the body. Aside from its direct action, the immune system's response is also influenced by other systems of the body including the nervous, respiratory, circulatory, and digestive systems.

One of the better-known aspects of the immune system is its ability to respond to foreign antigens presented by invading organisms, cellular changes within the body, or from vaccination. Some of the first kinds of cells that respond to such activation of the immune system are phagocytes and natural killer cells. Phagocytes include among other cells, monocytes, macrophages, and polymorphonuclear neutrophils. These cells generally bind to the foreign antigen, internalize it and often times destroy it. They also produce soluble molecules that mediate other immune responses, such as inflammatory responses. Natural killer cells can recognize and destroy certain virally-infected embryonic and tumor cells. Other factors of the immune response include complement pathways, which are capable of responding independently to foreign antigens or acting in concert with cells or antibodies.

One of the aspects of the immune system that is important for vaccination is the specific response of the immune system to a particular pathogen or foreign antigen. Part of the response includes the establishment of "memory" for that foreign antigen. Upon a secondary exposure, the memory function allows for a quicker and generally greater response to the foreign antigen. Lymphocytes in concert with other cells and factors play a major role in both the memory function and the response.

Generally, it is thought that the response to antigens involves both humoral responses and cellular responses. Humoral immune responses are mediated by non-cellular factors that are released by cells and which may or may not be found free in the plasma or intracellular fluids. A major component of a humoral response of the immune system is mediated by antibodies produced by B lymphocytes. Cell-mediated immune responses result from the interactions of cells, including antigen presenting cells and B lymphocytes (B cells) and T lymphocytes (T cells).

One of the most widely employed aspects of the immune response capabilities is the production of monoclonal antibodies. The advent of monoclonal antibody (Mab) technology in the mid 1970s provided a valuable new therapeutic and diagnostic tool. For the first time, researchers and clinicians had access to unlimited quantities of uniform antibodies capable of binding to a predetermined antigenic site and having various immunological effector functions. Currently, the techniques for production of monoclonal antibodies are well known in the art.

These monoclonal antibodies are thought to hold great promise in medicine and diagnostics. Unfortunately, the development of therapeutic products based on these proteins has been limited because of problems that are inherent in monoclonal antibody therapy. For example, most monoclonal antibodies are mouse derived and, thus, do not fix human complement well. They also lack other important immunoglobulin functional characteristics when used in humans.

The biggest drawback to the use of monoclonal antibodies is the fact that nonhuman monoclonal antibodies are immunogenic when injected into a human patient. After injection of a foreign antibody, the immune response mounted by a patient can be quite strong. The immune response causes the quick elimination of the foreign antibody, essentially eliminating the antibody's therapeutic utility after an initial treatment. Unfortunately, once the immune system is primed to respond to foreign antibodies, later treatments with the same or different nonhuman antibodies can be ineffective or even dangerous.

Mice can be readily immunized with foreign antigens to produce a broad spectrum of high affinity antibodies. However, the introduction of murine antibodies into humans results in the production of a human-anti-mouse antibody (HAMA) response due to the presentation of a mouse antibody in the human body. Use of murine antibodies in a patient is generally limited to a term of days or weeks. Longer treatment periods may result in anaphylaxis. Moreover, once HAMA has developed in a patient, it often prevents the future use of murine antibodies for diagnostic or therapeutic purposes.

To overcome the problem of HAMA response, researchers have attempted several approaches to modify nonhuman antibodies, to make them human-like. These approaches include mouse/human chimers, humanization, and primatization. Early work in making more human-like antibodies used combined rabbit and human antibodies. The protein subunits of antibodies, rabbit Fab fragments and human Fc fragments, were joined through protein disulfide bonds to form new, artificial protein molecules or chimeric antibodies.

Recombinant molecular biological techniques have been used to create chimeric antibodies. Recombinant DNA technology was used to construct a gene fusion between DNA sequences encoding mouse antibody variable light and heavy chain domains and human antibody light chain (LC) and heavy chain (HC) constant domains to permit expression of chimeric antibodies. These chimeric antibodies contain a large number of nonhuman amino acid sequences and are immunogenic to humans. Patients exposed to these chimeric antibodies produce human-anti-chimera antibodies (HACA). HACA is directed against the murine V region and can also be directed against the novel V-region/C-region (constant region) junctions present in recombinant chimeric antibodies.

To overcome some of the limitations presented by the immunogenicity of chimeric antibodies, molecular biology techniques are used to created humanized or reshaped antibodies. The DNA sequences encoding the antigen binding portions or complementarity determining regions (CDRs) of murine monoclonal antibodies are grafted, by molecular means, on the DNA sequences encoding the frameworks of human antibody heavy and light chains. The humanized Mabs contain a larger percentage of human antibody sequences than do chimeric Mabs. The end product, which comprises approximately 90% human antibody and 10% mouse antibody, contains a mouse binding-site on a human antibody. It also contains certain amino acid substitutions from the mouse Mab into the framework of the humanized Mab in order to retain the correct shape, and thus, binding affinity for the target antigen.

In practice, simply substituting murine CDRs for human CDRs is not sufficient to generate efficacious humanized antibodies retaining the specificity of the original murine antibody. There is an additional requirement for the inclusion of a small number of critical murine antibody residues in the human variable region. The identity of these residues depends upon the structure of both the original murine antibody and the acceptor human antibody. It is the presence of these murine antibody residues that helps create a HACA response in the patient, leading to rapid clearance of the monoclonal antibodies and the fear of anaphylaxis.

Another technique, called resurfacing technology, is used for humanizing mouse antibodies. Resurfacing involves replacing the mouse antibody surface with a human antibody surface in a process that is faster and more efficient than other humanization techniques. This technique provides a method of redesigning murine monoclonal antibodies to resemble human antibodies by humanizing only those amino acids that are accessible at the surface of the V-regions of the recombinant $F_v$. The resurfacing of murine monoclonal antibodies may maintain the avidity of the original mouse monoclonal antibody in the reshaped version, because the natural framework-CDR interactions are retained. Again, these antibodies suffer from the problem of being antigenic due to their mouse origins.

Other technologies use primate, rather than mouse, sequences to humanize Mabs. The rationale of this approach, called primatization, is that most of the sequences in the primate antibody variable region are indistinguishable from human sequences. Primatized anti-CD4 Mabs for the treatment of rheumatoid arthritis and severe asthma are being developed. However, these Mabs are still foreign proteins to the immune system of the patient and evoke an immune response.

In an effort to avoid the immune response to foreign proteins, a variety of approaches are being developed to make human Mabs that contain only human antibody components. One approach is to isolate a human B cell clone that naturally makes antibody to the desired antigen and to grow it in a trioma cell culture system. Because human antibodies are made only against antigens that are foreign to the host, none of the human B cells will make antibodies against human antigens. Therefore, this approach is not useful to produce Mabs against antigens that are human proteins.

Two other approaches to create human Mabs are phage display and use of transgenic mice. Phage display technique takes advantage of the ability of humans to make antibodies against any possible structure. This technique uses the antibody genes from many individual humans to create a large library of phage antibodies, each displaying a functional antibody variable domain on its surface. From this library, individual variable domains are selected for their ability to bind to the desired antigen. The Mab is created through molecular biology techniques by combining an antibody variable domain having the desired binding characteristics and a constant domain that best meets the potential human therapeutic product. Again, this technique lacks antigen specificity. The phage library cannot contain every binding region for any and all desired antigens. It also may contain binding regions, which lack specificity. Thus, this technique may require considerable engineering to increase antibody affinities to useful levels.

Transgenic mice are also being used to create "human" antibodies. The transgenic mice are created by replacing mouse immunoglobulin gene loci with human immunoglobulin loci. This approach may provide advantages over phage display technologies because it takes advantages of mouse in vivo affinity maturation machinery.

All of the current technologies for producing human or human-like Mabs are insufficient to provide a species-specific antibody that is antigen specific for a described antigen. Chimeric antibodies have the advantages of retaining the specificity of the murine antibody and stimulating human Fc dependent complement fixation and cell-mediated cytotoxicity. However, the murine variable regions of these chimeric antibodies can still elicit a HAMA response, thereby limiting the value of chimeric antibodies as diagnostic and therapeutic agents.

Vaccines may be directed at any foreign antigen, whether from another organism, a changed cell, or induced foreign attributes in a normal "self" cell. The route of administration of the foreign antigen can help determine the type of immune response generated. For example, delivery of antigens to mucosal surfaces, such as oral inoculation with live polio virus, stimulates the immune system to produce an immune response at the mucosal surface. Injection of antigen into muscle tissue often promotes the production of a long lasting IgG response.

Vaccines may be generally divided into two types, whole and subunit vaccines. Whole vaccines may be produced from viruses or microorganisms which have been inactivated or attenuated or have been killed. Live attenuated vaccines have the advantage of mimicking the natural infection enough to trigger an immune response similar to the response to the wild-type organism. Such vaccines generally provide a high level of protection, especially if administered by a natural route, and some may only require one dose to confer immunity. Another advantage of some attenuated vaccines is that they provide person-to-person passage among members of the population. These advantages, however, are balanced with several disadvantages. Some attenuated vaccines have a limited shelf-life and cannot withstand storage in tropical environments. There is also a possibility that the vaccine will revert to the virulent wild-type of the organism, causing harmful, even life-threatening, illness. The use of attenuated vaccines is contraindicated in immunodeficient states, such as AIDS, and in pregnancy.

Killed vaccines are safer in that they cannot revert to virulence. They are generally more stable during transport and storage and are acceptable for use in immunocompromised patients. However, they are less effective than the live attenuated vaccines, usually requiring more than one dose. Additionally, they do not provide for person-to-person passage among members of the population.

Production of subunit vaccines requires knowledge about the epitopes of the microorganism or cells to which the vaccine should be directed. Other considerations in designing subunit vaccines are the size of the subunit and how well the subunit represents all of the strains of the microorganism or cell. The current focus for development of bacterial vaccines has shifted to the generation of subunit vaccines because of the problems encountered in producing whole bacterial vaccines and the side effects associated with their use. Such vaccines include a typhoid vaccine based upon the Vi capsular polysaccharide and the Hib vaccine to Haemophilus influenzae.

Because of the safety concerns associated with the use of attenuated vaccines and the low efficacy of killed vaccines, there is a need in the art for compositions and methods that enhance vaccine efficacy. There is also a need in the art for compositions and methods of enhancing the immune system, which stimulate both humoral and cell-mediated responses. There is a further need in the art for the selective adjustment of an immune response and manipulating the various components of the immune system to produce a desired response. Additionally, there is a need for methods and compositions that can accelerate and expand the immune response for a more rapid activation response. There is an increased need for the ability to vaccinate populations, of both humans and animals, with vaccines that provide protection with just one dose.

What is needed are compositions and methods to target the delivery of specific agents to only the target cells. Such compositions and methods should be able to deliver therapeutic agents to the target cells efficiently. What is also needed are compositions and methods that can be used both in in vitro and in vivo systems.

There is also a general need for compositions of monoclonal antibodies and improved methods for producing them. There is a particular need for methods for producing human antibodies having affinity for a predetermined antigen. These human immunoglobulins should be easily and economically produced in a manner suitable for therapeutic and diagnostic formulation.

SUMMARY OF THE INVENTION

The present invention comprises compositions and methods for making species-specific antigen-specific monoclonal antibodies, preferably IgG monoclonal antibodies. The present invention further comprises vectors that replicate elements of the immune system, particularly the antigen-presenting cell (APC) element of the immune synapse. A preferred vector optionally comprises binding an antigen-loaded major histocompatibility (MHC) class II protein, the co-stimulatory protein B7, and the structural protein intracellular adhesion protein (I-CAM) onto the surface of colloidal metal vectors. Such vectors replicate the 3-D orientation of the APC (FIG. 3) generating a synthetic antigen-presenting cell (sAPC) capable of activating $CD4^+$ T-cells to mature the antibody response of immunized B-cells.

The present invention further comprises vectors, including a synthetic $CD4^+$ T-cell (sTc), and a synthetic germinal center (sGC). In one embodiment the synthetic $CD4^+$ T-cell is comprised of colloidal metal vectors bound with CD40 ligand and cytokines. In another embodiment the synthetic germinal center is comprised of colloidal metal vectors bound with B Lymphocyte Stimulator; BlyS and CD30L/receptor system, that increase the efficiency and specificity of B-cell antibody response to in vitro immunization. While not wishing to be bound to any particular theory, in one embodiment the physical juxtaposition of the antigen with B-cell growth factors improves the uptake of the human TNF antigen through the surface IgM antigen receptor and induces a more robust B-cell response. Having these signals juxtaposed on the same B-cell further improves the ability to elicit an antigen specific B-cell response in vitro.

The present invention comprises methods of making the synthetic immune component elements. Methods are taught herein for making vector compositions that mimic the functionality of components of the immune system. The present invention also comprises methods of treatment of immune system-related diseases and pathologies. Methods of vaccination are also included in the present invention.

DETAILED DESCRIPTION OF THE INVENTION

Figure 1:
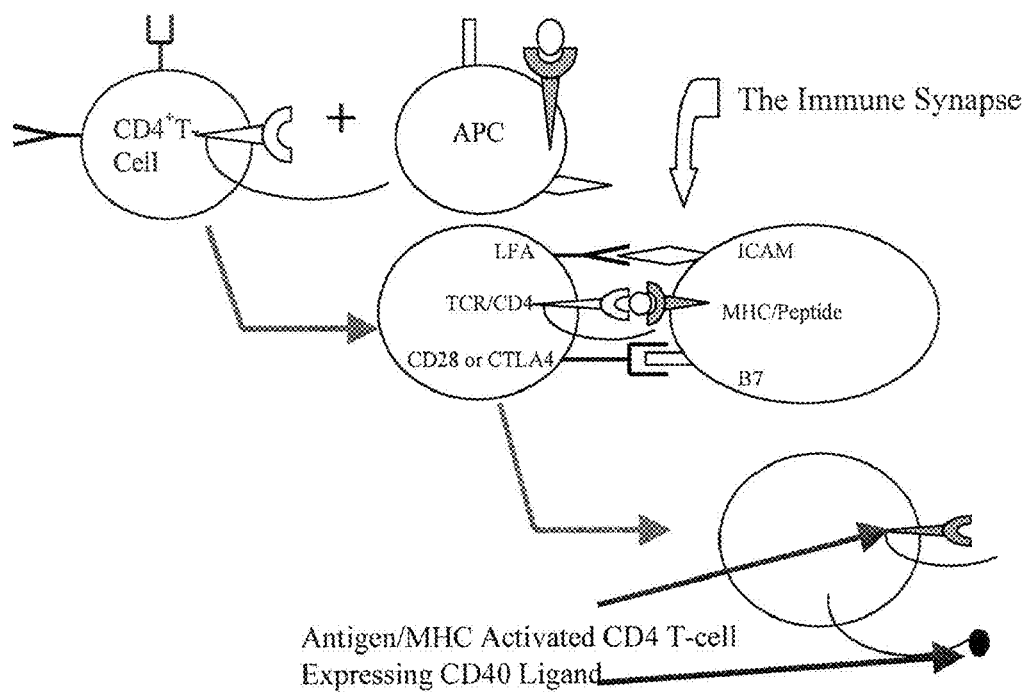
FIG. 1 provides a schematic representation of the immune synapse.

The present invention may be understood more readily by reference to the following detailed description of specific embodiments included herein. Although the present invention has been described with reference to specific details of certain embodiments, thereof, it is not intended that such details should be regarded as limitations upon the scope of the invention. The entire text of the references mentioned herein are hereby incorporated in their entireties by reference, including U.S. Provisional Application Ser. No. 60/526,360.

The present invention comprises methods and compositions for generating antigen specific, species-specific IgG monoclonal antibodies. The present invention comprises methods and compositions comprising naturally occurring and/or synthetic vectors that replicate the antigen-presenting cell (APC), T cell and germinal center elements of the humoral immune response.

The present invention comprises vectors that mimic any of the elements or stages of the immune response. The immune response is initiated by the recognition of foreign antigens by various kinds of cells, principally macrophages or other antigen presenting cells. This leads to activation of lymphocytes, in particular, the lymphocytes that specifically recognize that particular foreign antigen and results in the development of the immune response, and possibly, elimination of the foreign antigen. Overlaying the immune response directed at elimination of the foreign antigen are complex interactions that lead to helper functions, stimulator functions, suppresser functions and other responses. The power of the immune system's responses must be carefully controlled at multiple sites for stimulation and suppression or the response will either not occur, over respond, or not cease after elimination.

The recognition phase of response to foreign antigens consists of the binding of foreign antigens to specific receptors on immune cells. These receptors generally exist prior to antigen exposure. Recognition can also include interaction with the antigen by macrophage-like cells or by recognition by factors within serum or bodily fluids.

In the activation phase, lymphocytes undergo at least two major changes. They proliferate, leading to expansion of the clones of antigen-specific lymphocytes and amplification of the response, and the progeny of antigen-stimulated lymphocytes differentiate either into effector cells or into memory cells that survive, ready to respond to re-exposure to the antigen. There are numerous amplification mechanisms that enhance this response.

In the effector phase, activated lymphocytes perform the functions that may lead to elimination of the antigen or establishment of the vaccine response. Such functions include cellular responses, such as regulatory, helper, stimulator, suppressor or memory functions. Many effector functions require the combined participation of cells and cellular factors. For instance, antibodies bind to foreign antigens and enhance their phagocytosis by blood neutrophils and mononuclear phagocytes. Complement pathways are activated and may participate in the lysis and phagocytosis of microbes in addition to triggering other body responses, such as fever.

In the immune response to antigens, immune cells interact with each other by direct cell-to-cell contact or indirect cell-to-cell (factor mediated) communication. For example, interactions between T cells, macrophages, dendritic cells, and B cells are necessary for an effective immune response. Antigen-presenting cells (APC) activate B and T cells by presenting them B and T cells with processed antigens and other activation signals. Activated T cells help control immune responses and participate in the removal of foreign organisms. Helper T cells cause cells to become better effector cells, such as helping cytotoxic T cell precursors to develop into killer cells, helping B cells make antibodies, and helping increase functions of other cells like macrophages. Activated B cells divide and produce antigen specific antibodies and memory B cells. The cells involved in the immune response also secrete cellular factors or cytokines, which enhance the functions of phagocytes, stimulate inflammatory responses and affect a variety of cells.

The reactions of these cells also involve feedback loops. Macrophages and other mononuclear phagocytes, or APCs, actively phagocytose antigens for presentation to B and T cells and such activity can be enhanced by lymphocytic cellular factors. Macrophages also produce cytokines that, among other activities, stimulate T cell proliferation and differentiation, recruit other inflammatory cells, especially neutrophils, and are responsible for many of the systemic effects of inflammation, such as fever. One such cytokine, called interleukin-12, is especially important for the development of cell-mediated immunity.

Dendritic cells are also APCs, which initiate an immune response. There are a number of different types of dendritic cells, including lymphoid dendritic cells and Langerhans cells of the skin. They can be found throughout the body and particularly in the spleen, lymph nodes, tonsils, Peyer's patches, and thymus. They are irregularly shaped cells, which continuously extend and contract dendritic (tree-like) processes. One of their roles in the immune system is to induce and regulate B and T cell activation and differentiation. They are potent accessory cells for the development of cytotoxic T cells, antibody formation by B cells, and some polyclonal responses like oxidative mitogenesis. They also stimulate T cells to release the cytokine interleukin-2

An important arm of vaccination is the response to antigens that is provided by B lymphocytes or B cells. B cells represent about 5 to 15% of the circulating lymphocytes. B cells produce immunoglobulins, IgG, IgM, IgA, IgD, and IgE, which may be released into body fluids, secreted with attached proteins or be inserted into the surface membrane of the B cell. Such immobilized immunoglobulins act as specific antigen receptors. In responding to antigen, these immunoglobulin receptors are crosslinked at a specific site on the B cell. This process, which is known as capping, is followed by internalization and degradation of the immunoglobulin. In APCs, which may include B cells, antigen fragments are combined with the MHC and ultimately expressed on the surface of the APC.

The B plasma cells produce and secrete antibody molecules that can bind foreign proteins, polysaccharides, lipids, or other chemicals in extracellular or cell-associated forms. The antibodies produced by a single plasma cell are specific for one antigen. The secreted antibodies bind the antigen and trigger the mechanisms that facilitate their destruction.

In 1975, Kohler and Milstein (Kohler, G., and Milstein, C., Nature (London). 1975. volume 256: pp-495) described a method for fusing antibody-producing B cells isolated from the spleens of immunized mice with aggressively proliferating mouse myeloma cells. This resultant hybrid cell, a hybridoma, possesses the characteristics of both parental cells. It produces and secretes large amounts of antibody during its continued growth and proliferation. Through a series of systematic cellular dilutions, genetically singular hybridoma cells can be isolated that produce an antibody of singular specificity, a monoclonal antibody (Mab).

The most common procedures require that the production of monoclonal antibodies start with the immunization of an animal. Antigen, draining into a local lymph node or spleen, activates naïve B-cells to produce IgM antibodies. These activated B cells are then presented with antigen-activated CD4$^+$ T cells to induce class switching. Class switching is characterized by a change in the production of antibody type from IgMs to IgGs (Kuby, J., Immunology Third Edition 1997. eds Allen D., pp-205-213). Antibody secreting B cell lymphocytes are isolated from the lymph node or spleen of the immunized animal, and are fused with species-specific myeloma cells. The fused cells are then allowed to grow to produce antigen specific IgG antibodies. During the screening process, positive fusion clones are selected for their therapeutic potential.

Mice can be readily immunized with foreign antigens to produce a broad spectrum of high affinity antibodies. However, the introduction of murine antibodies into humans results in the production of a human-anti-mouse antibody (HAMA) response due to the presentation of a foreign protein in the body. Use of murine antibodies in a patient is generally limited to a term of days or weeks. Moreover, once HAMA has developed in a patient, it often prevents the future use of murine antibodies for other diagnostic or therapeutic purposes.

The early success of this technology in animals prompted scientists in the 1980's to extend this concept and attempt to produce human monoclonal antibodies. However, extrapolation from animal to human was fraught with difficulties. The first hurdle was the lack of antigen specific B cells. Standard monoclonal antibody procedure requires that these cells be harvested from an animal that had been immunized, a method not generally applicable to humans. This problem is further compounded by (i) the fact that there is no ready source of activated B cells, (ii) the paucity of immune competent B cells present in peripheral blood, and (iii) the inability to obtain either lymph nodes or spleens from human subjects. These factors prompted the development of a variety in vitro strategies to produce human monoclonal antibodies. Although initial results showed great promise, the inability to completely reconstruct the sequence of events of the in vivo antibody response ultimately caused the technology to fail and this technical approach has been essentially abandoned.

The first barrier to in vitro antibody production is the relatively low conversion rate of naïve human B cell lymphocytes to activated B cells. In the past resolving this challenge proved difficult even when recall antigens, such as Tetanus toxin (Butler et. al., J. Immuol. 1983. volume 130: pp-165), were used to induce a primary antibody response from human peripheral blood B cell lymphocytes. The present invention comprises methods for making vectors that activate pathways that lead to antibody generation. The present invention also comprises compositions of naturally occurring or synthetic vectors. Such vectors comprise colloidal gold platforms with multiple B cell ligands associated.

Numerous examples of cross-linking of receptor/ligand pairs to potentiate biologic responses have been described (Carroll, K., Prosser, E., and Kennedy, R. Hybridoma 1991. 10: 229-239). The present invention comprises vectors of colloidal metal that increase the efficiency and specificity of B cell antibody response to in vitro immunization. Though not wishing to be bound by any particular theory, it is believed that the physical juxtaposition of the antigen with B cell growth factors improves the uptake of the antigen through the surface IgM antigen receptor and induces a more robust B cell response. There is also improved antigen processing and presentation. Having these signals juxtaposed on the same B cell improves the ability to elicit an antigen specific B cell response in vitro.

In one embodiment, the component-specific immunostimulating molecule and/or MHC protein and/or the antigen may be bound directly to the colloidal metal platform or may be bound to the colloidal metal platform through members of a binding group. Such binding groups may comprise free sulfhydryl or pyridyl groups present on, or synthetically added to the immune component. A preferred embodiment of the present invention comprises a colloidal metal as a platform that is capable of binding a member of a binding group to which a component-specific immunostimulating agent, or a MHC protein or an antigen are bound to create a synthetic APC. In an alternatively preferred embodiment, the binding group is streptavidin/biotin and the component-specific immunostimulating agent is a cytokine Embodiments of the present invention may also comprise binding the antigen, or the MHC protein or the component-specific immunostimulating agent in a less specific method, without the use of binding partners, such as by using polycations or proteins. As such, the present invention contemplates the use of interacting molecules such as polycationic elements known to those skilled in the art including, but not limited to, polylysine, protamine sulfate, histones or asialoglycoproteins.

The members of the binding pair comprise any such binding pairs known to those skilled in the art, including but not limited to, antibody-antigen pairs, enzyme-substrate pairs; receptor-ligand pairs; and streptavidin-biotin. Novel binding partners may be specifically designed. An essential element of the binding partners is the specific binding between one of the binding pair with the other member of the binding pair, such that the binding partners are capable of being joined specifically. Another desired element of the binding members is that each member is capable of binding or being bound to either an integrating molecule or a targeting molecule.

The compositions of the invention comprise a colloidal metal, an antigen, and a component specific immunostimulating agent. Alternatively, compositions of the invention comprise a colloidal metal, a MHC protein, an antigen, and a component specific immunostimulating agent. The component specific immunostimulating agent may comprise biologically active agents that can be used in therapeutic applications or the component specific immunostimulating agent may be useful in detection methods. In additional embodiments, one or more component specific immunostimulating agents are admixed, associated with or bound directly or indirectly to the colloidal metal. Admixing, associating and binding includes covalent and ionic bonds and other weaker or stronger associations that allow for long term or short term association of the derivatized-PEG or the derivatized poly-l-lysine, component specific immunostimulating agents, and other components with each other and with the colloidal metal particles.

In yet another embodiment, the compositions may also comprise one or more targeting molecules admixed, associated or bound to the colloidal metal. The targeting molecule can be bound directly or indirectly to the metal particle. Indirect binding includes binding through molecules such as polylysines or other integrating molecules or any association with a molecule that binds to both the targeting molecule and either the metal sol or another molecule bound to the metal sol.

Of particular interest are detection agents such as dyes or radioactive materials that can be used for visualizing or detecting the sequestered colloidal metal vectors. Fluorescent, chemiluminescent, heat sensitive, opaque, beads, magnetic and vibrational materials are also contemplated for use as detectable agents that are associated or bound to colloidal metals in the compositions of the present invention.

Generation of a primary antibody response from naïve human B cells in vitro represents only the first step in the in vitro reconstruction of the human antibody response. The primary antibody response from immunized human B cells results in the secretion of IgM antibodies. A second class of lymphoid cells, known as antigen presenting cells (APCs), also internalizes the antigen. Once internalized these cells process the protein antigen into fragments, which are then expressed on the cell's surface bound to one of two major histocompatibility complexes (MHCs). These cells are important for antibody class switching.

A current theory of immune system responses is herein presented. The present invention is not limited to the mechanisms described herein, but can function in multiple methods, not limited by any particular theory described herein. Depending on the microenvironment, APCs expressing antigen bound to class II MHC molecules activate one of two subsets of CD4+ T cells. These cells, also known as helper T cells, perform the necessary accessory functions to facilitate the cellular or the humoral (antibody) immune response. $T_H1$ CD4+ cells facilitate the cellular immune response, while the $T_H2$ subset of CD4+ cells interact with IgM secreting B cells to initiate the process of class switching.

The activation of CD4+ $T_H2$ T-cells by the APC occurs with the formation of a bicellular cleft known as the immune synapse (Wulfing C, Sumen C, Sjaastad M D, Wu L C, Dustin M L, Davis M M. Nat Immunol 2002. 31: 42-7). The formation of the immune synapse involves interaction and rearrangement of signaling and structural ligands on the APC with their respective receptors on the T cell to form a three-dimensional (3-D) bridge that allows contact and signaling between these two cells (FIG. 1). Antigen signaling between the APC and the T cell occurs through the binding of the MHC/antigen complex with the T cell receptor complex, while the structural integrity of the immune synapse is maintained by the interaction of ICAM (intracellular adhesion molecule), LFA-3, and CD72 on the APC with LFA-1, CD2, and CD5 receptors on T cells, respectively. The successful formation of the immune synapse causes the CD4+ T cell to express a B cell stimulatory molecule known as CD40 ligand.

Figure 2:
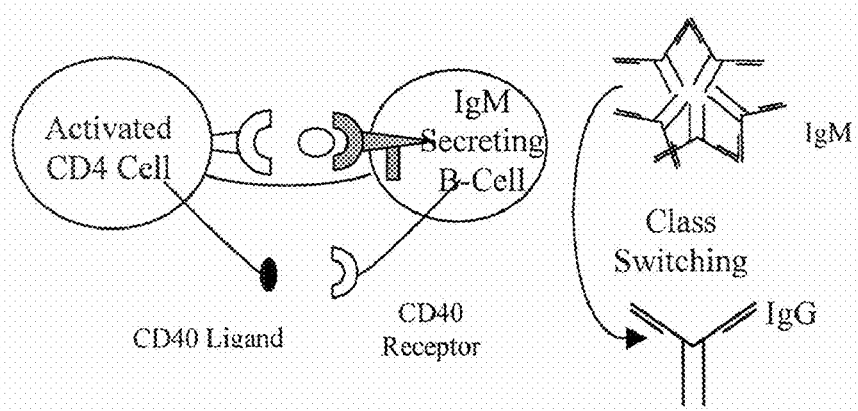
FIG. 2 provides a schematic representation of the differentiation of primary antibody response by activated $CD4^+$ T-cell.

The formation of the immune synapse may signal the T cell to become active or inactive (anergic). Which response is initiated is dependent on the strength of the co-stimulatory signals provided by the B7 molecule on the APC to the T cell. The B7 molecule may interact with either B7 receptor molecule on the T cell, CD28 or CTLA4. These B7 receptors differ with respect to their density on the surface of the T cell as well as their affinity for the B7 molecule. CD28 has a lower affinity for B7 than CTLA4, but is present at a much higher density on the surface of the T cell. The binding of B7 to the CD28 receptor sends an activation signal to the T cell, while the binding of B7 by CTLA4 induces T cell anergy (Kuby, J., Immunology Third Edition 1997. eds Allen D., pp. 213-218). Thus, presenting excess B7 in the immune synapse will ensure that the T cells will be activated. The activated CD4+/CD40+ T cell forms a synapse with an IgM secreting B cell. The interaction of CD40 ligand on the T cell with the CD40 receptor on the B cell causes the IgM secreting B cell to undergo class switching to produce IgGs (FIG. 2).

Figure 3:
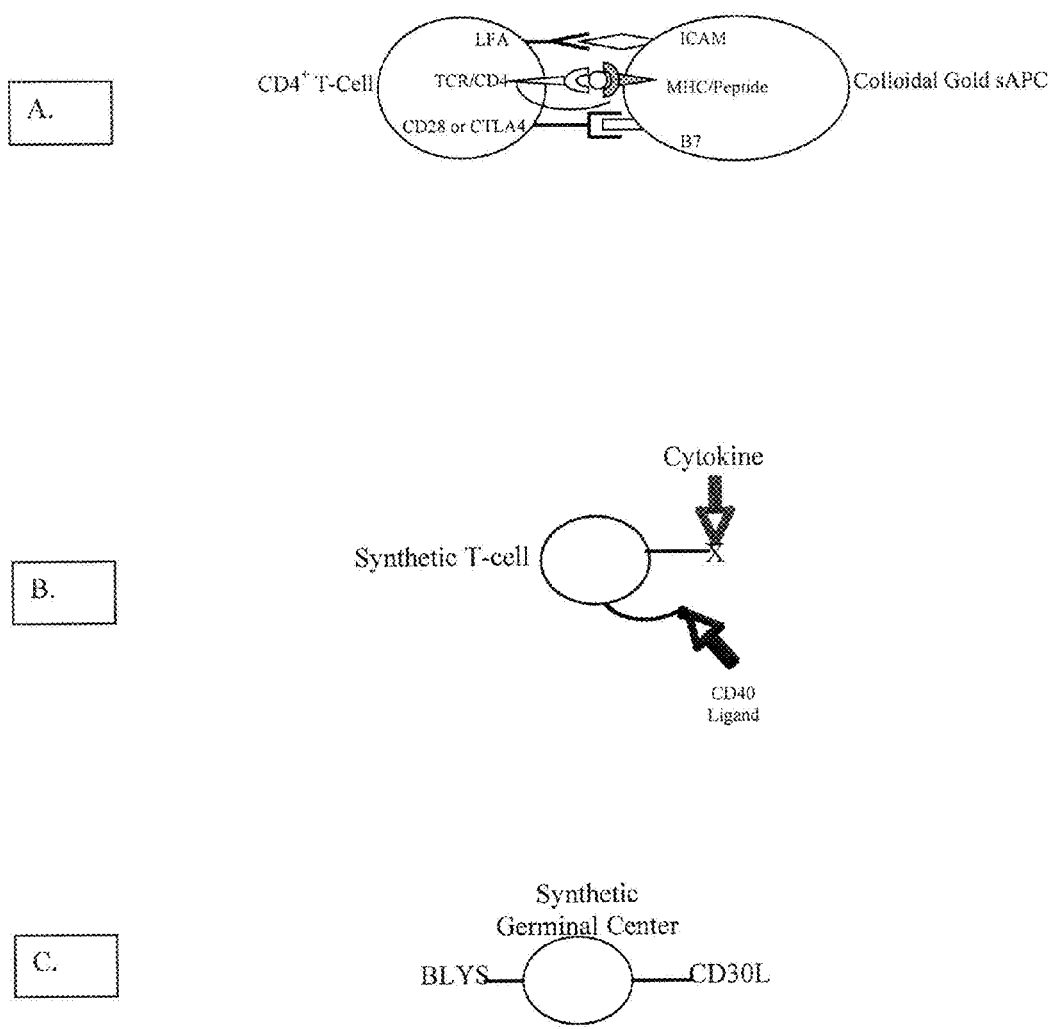
FIG. 3A provides a schematic of the colloidal gold synthetic antigen-presenting cell.
FIG. 3B provides a schematic of the colloidal gold synthetic T-Cell.
FIG. 3C provides a schematic of the colloidal gold synthetic germinal center.
Figure 4:
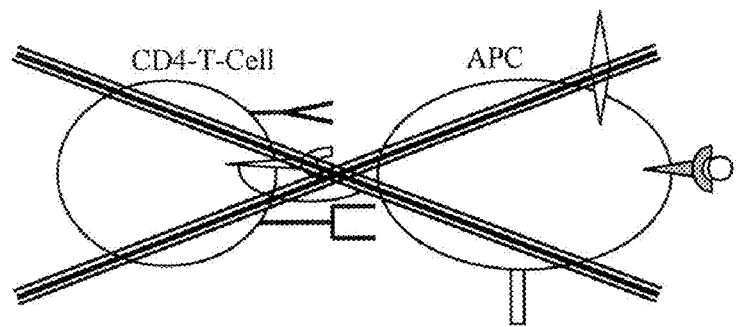
FIG. 4 provides a schematic representation of the inability of a single particle sAPC to form a functional immune synapse.

The present invention comprises methods of making sAPCs capable of activating CD4+T cells, and synthetic CD4+ T-cells (sTc) and synthetic germinal centers (sGC) able to mature the antibody response of immunized B cells or immortalized B cells. The compositions of the present invention comprise colloidal metal vectors capable of activating T cells and vectors that cause the maturation of immunized or immortalized B cells. For example, a vector may have an antigen-loaded major histocompatibility (MHC) class II protein, the co-stimulatory protein B7, and a structural protein such as intracellular adhesion molecule (ICAM), LFA-3 and CD72, associated with the surface of colloidal metal vectors. This vector replicates the 3-D orientation of the APC (FIG. 3) and functions as a synthetic antigen-presenting cell (sAPC) capable of activating CD4+ T cells to mature the antibody response of immunized B cells. One embodiment of the sAPC comprises all of the components on a single particle of colloidal metal. Another embodiment of the sAPC comprises the constituent proteins of the immune synapse bound on separate particles of colloidal gold that self-assemble in vitro to form the sAPC.

The methods and compositions of the present invention comprising synthetic antigen-presenting cells (sAPC) comprise compositions that are readily available and can be "pulled out of the refrigerator" and used to manipulate the human antibody response. Thus the present invention comprises methods of treatment of diseases and immune related dysfunctions and pathologies. The colloidal metal compositions provide control over the variables that are responsible for initiating, maintaining and regulating the immune response (either down-regulating or up-regulating), such as particle size, the amount of protein bound per particle, the flexibility of protein movement on the particle, as well as the 3-D assembly of the particles, ensures reproducible control of the sAPC.

The vector compositions of the present invention can be used in in vitro production of monoclonal antibodies. Such monoclonal antibodies can be used in methods of treatment for multiple diseases. The vector compositions of the present invention can also be used in making improved vaccine compositions.

In vaccine therapy, compositions of synthetic immunogens specifically designed to stimulate both the cellular and humoral responses of the human immune system are used. By creating specific synthetic cellular immune elements for the presentation of the antigen and stimulation of specific cells, a more predictable and efficient vaccine response is enabled.

The present invention comprises combination vaccines and DNA vaccines. An example of a combination vaccine is the *Bordetella pertussis* toxin and its surface fimbrial hemaglutinin. In DNA vaccination, the patient is administered nucleic acids encoding a protein antigen that is then transcribed, translated and expressed in some form to produce strong, long-lived humoral and cell-mediated immune responses to the antigen.

The immune response created by vaccines can be non-specifically enhanced by the use of adjuvants. These are a heterogeneous group of compounds or carrier components, such as liposomes, emulsions or microspheres, with several different mechanisms of action. Methods of the present invention comprise use of vaccines for protection against disease, and to treat cancer.

Many diseases, in addition to cancer, are mediated by the immune system and the present invention comprises methods of treatment of such diseases by the administration of an effective amount of a composition comprising a colloidal metal vector that is capable of stimulating the immune system and its components. The diseases include, Crohn's disease, psoriasis, inflammatory bowel disease, adult respiratory distress syndrome, allergies, eczema, rhinitis, urticaria, anaphylaxis, transplant rejection, such as kidney, heart, pancreas, lung, bone, and liver transplants; rheumatic diseases, systemic lupus erthematosus, rheumatoid arthritis, seronegative spondylarthritides, Sjogren's syndrome, systemic sclerosis, polymyositis, dermatomyositis, type 1 diabetes mellitus, acquired immune deficiency syndrome, hand foot and mouth disease, Hashimoto's thyroiditis, Graves' disease, Addison's disease, polyendocrine autoimmune disease, hepatitis, sclerosing cholangitis, primary biliary cirrhosis, pernicious anemia, coeliac disease, antibody-mediated nephritis, glomerulonephritis, Wegener's granulomatosis, microscopic polyarteritis, polyarteritis nodosa, pemphigus, dermatitis herpetiformis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, Bruton's syndrome, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, and non-Hodgkin's lymphoma.

The present methods enhance vaccine effectiveness by targeting specific immune components for activation. Compositions comprising component-specific immunostimulating agents in association with colloidal metal and antigen are used. Examples of diseases for which vaccines are currently available include, but are not limited to, cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough, and yellow fever.

The combination of route of administration and the vectors used to deliver the antigen to the immune system is a powerful tool in designing the desired immune response. The present invention comprises methods and compositions comprising various vectors or vectors in association with delivery agents, such as liposomes, microcapsules, or microspheres that can provide long-term release of immune stimulating vector compositions. These delivery systems act like internal depots for holding the vector and slowly releasing it for immune system activation. For example, a liposome may be filled with a composition comprising a vector comprising an antigen and component-specific immunostimulating agents associated with colloidal metal.

The antigen/component-specific immunostimulating agent/metal complex is slowly released from the liposome and is recognized by the immune system as foreign and the specific component to which the component-specific immunostimulating agent is directed activates the immune system. The cascade of immune response is activated more quickly by the presence of the component-specific immunostimulating agent and the immune response is generated more quickly and more specifically.

Other methods and compositions contemplated in the present invention include using antigen/component-specific immunostimulating agent/colloidal metal complexes in which the colloidal metal particles have different sizes. Sequential administration of component-specific immunostimulating agents may be accomplished in a one-dose administration by the use of these differently sized colloidal metal particles. One dose would include four independent component-specific immunostimulating agents complexed to an antigen and each with a differently sized colloidal metal particle. Thus, simultaneous administration would provide sequential activation of the immune components to yield a more effective vaccine and more protection for the population. Other types of such single dose administration with sequential activation could be provided by combinations of differently sized colloidal metal particles and liposomes or liposomes filled with differently sized colloidal metal particles.

Use of such a vaccination system as described above is very important in providing vaccines that can be administered in one dose. One dose administration is important in treating animal populations such as livestock or wild populations of animals. One dose administration is vital in treatment of populations that are resistant to healthcare such as the poor, homeless, rural residents or persons in developing countries that have inadequate health care. Many persons, in all countries, do not have access to preventive types of health care, such as vaccination. The re-emergence of infectious diseases, such as tuberculosis, has increased the demand for vaccines that can be given once and still provide long-lasting, effective protection. The compositions and methods of the present invention provide such effective protection.

The term "colloidal metal," as used herein, includes any water-insoluble metal particle or metallic compound as well as colloids of non-metal origin such as colloidal carbon dispersed in liquid or water (a hydrosol). Examples of colloidal metals, which can be used in the present invention include, but are not limited to, metals in groups IIA, IB, IIB and IIIB of the periodic table, as well as the transition metals, especially those of group VIII. Preferred metals include gold, silver, aluminum, ruthenium, zinc, iron, nickel and calcium. Other suitable metals may also include the following in all of their various oxidation states: lithium, sodium, magnesium, potassium, scandium, titanium, vanadium, chromium, manganese, cobalt, copper, gallium, strontium, niobium, molybdenum, palladium, indium, tin, tungsten, rhenium, platinum, and gadolinium. The metals are preferably provided in ionic form (preferably derived from an appropriate metal compound), for example, the $Al^{3+}$, $Ru^{3+}$, $Zn^{2+}$, $Fe^{3+}$, $Ni^{2+}$ and $Ca^{2+}$ ions. A preferred metal is silver, particularly in a sodium borate buffer, having the concentration of between approximately 0.1% and 0.001%, and most preferably as approximately a 0.01% solution. Another preferred metal is gold, particularly in the form of $Au^{3+}$. An especially preferred form of colloidal gold is HAuCl4 (OmniCorp, South Plainfield, N.J.). The color of such a colloidal silver solution is yellow and the colloidal particles may range from 1 to 100 nanometers. Such metal ions may be present in the complex alone or with other inorganic ions.

Any antigen may be used in the present invention. Examples of antigens useful in the present invention include, but are not limited to, Interleukin-1 ("IL-1"), Interleukin-2 ("IL-2"), Interleukin-3 ("IL-3"), Interleukin-4 ("IL-4"), Interleukin-5 ("IL-5"), Interleukin-6 ("IL-6"), Interleukin-7 ("IL-7"), Interleukin-8 ("IL-8"), Interleukin-10 ("IL-10"), Interleukin-11 ("IL-11"), Interleukin-12 ("IL-12"), Interleukin-13 ("IL-13"), lipid A, phospholipase A2, endotoxins, staphylococcal enterotoxin B, Pertussis toxin, Tetanus toxin and other toxins, Type I Interferon, Type II Interferon, Tumor Necrosis Factor (TNF-α or b), Transforming Growth Factor-β ("TGF-β"), Lymphotoxin, Migration Inhibition Factor, Granulocyte-Macrophage Colony-Stimulating Factor ("CSF"), Monocyte-Macrophage CSF, Granulocyte CSF, vascular epithelial growth factor ("VEGF"), Angiogenin, transforming growth factor ("TGF-α"), heat shock proteins, Epidermal growth factor ("EGF"), carbohydrate moieties of blood groups, Rh factors, fibroblast growth factor, and other inflammatory and immune regulatory proteins, nucleotides, DNA, RNA, mRNA, sense, antisense, cancer cell specific antigens; such as MART, MAGE, BAGE, and heat shock proteins (HSPs); mutant p53; tyrosinase; mucines, such as Muc-1, PSA, TSH, autoimmune antigens; immunotherapy drugs, such as AZT; and angiogenic and anti-angiogenic drugs, such as angiostatin, endostatin, basic fibroblast growth factor, and vascular endothelial growth factor, prostate specific antigen and thyroid stimulating hormone.

The component-specific immunostimulating agent may be any molecule or compound which effects the immune system, for example, any molecule that increases the APC's ability to stimulate the B cell's production of antibodies. Examples of component-specific immunostimulating agents include, but are not limited to, antigens, colloidal metals, adjuvants, receptor molecules, nucleic acids, immunogenic proteins, and accessory cytokine/immuostimulators, pharmaceuticals, chemotherapy agents, and carriers.

Any type of pharmaceutical agent can be employed in the present invention. For example, anti-inflammatory agents such as steroids and nonsteroidal anti-inflammatory agents, soluble receptors, antibiotics, analgesic, COX-2 inhibitors. Chemotherapeutic agents of particular interest include the following non-limiting examples, taxol, paclitaxel, taxanes, vinblastin, vincristine, doxorubicin, acyclovir, cisplatin, methotrexate, mithramycin and tacrine.

These component-specific immunostimulating agents may be employed separately, or in combinations. They may be employed in a free state or in complexes, such as in combination with a colloidal metal.

Examples of component-specific immunostimulating agents useful in the present invention include, but are not limited to, Interleukin-1 ("IL-1"), Interleukin-2 ("IL-2"), Interleukin-3 ("IL-3"), Interleukin-4 ("IL-4"), Interleukin-5 ("IL-5"), Interleukin-6 ("IL-6"), Interleukin-7 ("IL-7"), Interleukin-8 ("IL-8"), Interleukin-10 ("IL-10"), Interleukin-11 ("IL-11"), Interleukin-12 ("IL-12"), Interleukin-13 ("IL-13"), lipid A, phospholipase A2, endotoxins, staphylococcal enterotoxin B and other toxins, Type I Interferon, Type II Interferon, Tumor Necrosis Factor ("TNF-α"), Flt-3 ligand, Transforming Growth Factor-β ("TGF-β") Lymphotoxin, Migration Inhibition Factor, Granulocyte-Macrophage Colony-Stimulating Factor ("CSF"), Monocyte-Macrophage CSF, Granulocyte CSF, vascular epithelial growth factor ("VEGF"), Angiogenin, transforming growth factor ("TGF-α"), heat shock proteins, carbohydrate moieties of blood groups, Rh factors, fibroblast growth factor, and other inflammatory and immune regulatory proteins, nucleotides, DNA, RNA, mRNA, sense, antisense, cancer cell specific antigens; such as MART, MAGE, BAGE, and heat shock proteins (HSPs); mutant p53; tyrosinase; autoimmune antigens; immunotherapy drugs, such as AZT; and angiogenic and anti-angiogenic drugs, such as angiostatin, endostatin, basic fibroblast growth factor, vascular endothelial growth factor (VEGF) and prostate specific antigen and thyroid stimulating hormone.

Adjuvants useful in the invention include, but are not limited to, heat killed *M. Butyricum* and *M. Tuberculosis*. Non-limiting examples of nucleotides are DNA, RNA, mRNA, sense, and antisense. Examples of immunogenic proteins include, but are not limited to, KLH (Keyhole Limpet Cyanin), thyroglobulin, and fusion proteins, which have adjuvant and antigen moieties encoded in the gene.

Component-specific immunostimulating agents may be delivered in their nucleic acid form, using known gene therapy methods, and produce their effect after translation. Additional elements for activation of immune components, such as antigens, could be delivered simultaneously or sequentially so that the cellularly translated component-specific immunostimulating agents and externally added elements work in concert to specifically target the immune response.

An especially preferred embodiment provides methods for activation of the immune response using vector compositions comprising agents comprised of a specific antigen in combination with a component-specific immunostimulating agent. Such methods are effective and can be used in in vitro or in vivo. As used herein, component-specific immunostimulating agent means an agent that is specific for a component of the immune system, such as a B or T cell, and that is capable of affecting that component, so that the component has an activity in the immune response. The component-specific immunostimulating agent may be capable of affecting several different components of the immune system, and this capability may be employed in the methods and compositions of the present invention. The agent may be naturally occurring or can be generated or modified through molecular biological techniques or protein receptor manipulations.

The activation of the component in the immune response may result in a stimulation or suppression of other components of the immune response, leading to an overall stimulation or suppression of the immune response. For ease of expression, stimulation of immune components is described herein, but it is understood that all responses of immune components are contemplated by the term stimulation, including but not limited to stimulation, suppression, rejection and feedback activities.

The immune component that is affected may have multiple activities, leading to both suppression and stimulation or initiation or suppression of feedback mechanisms. The present invention is not to be limited by the examples of immune responses detailed herein, but contemplates component-specific effects in all aspects of the immune system.

The activation of each of the components of the immune system may be simultaneous, sequential, or any combination thereof. In one embodiment of a method of the present invention, multiple component-specific immunostimulating agents are administered simultaneously. In this method, the immune system is simultaneously stimulated with multiple separate preparations, each containing a vector composition comprising a component-specific immunostimulating agent. Preferably, the vector composition comprises the component-specific immunostimulating agent associated with the colloidal metal. More preferably, the composition comprises the component-specific immunostimulating agent associated with the colloidal metal of one sized particle or of different sized particles and an antigen. Most preferably, the composition comprises the component-specific immunostimulating agent associated with the colloidal metal of one sized particle or of differently sized particles, an antigen and PEG or PEG derivatives, preferably thiol-PEG ($PEG(SH)_n$), or derivatized poly-l-lysine, preferably poly-l-lysine thiol ($PLL(SH)_n$).

Component-specific immunostimulating agents provide a specific stimulatory, up regulation, effect on individual immune components. For example, Interleukin-1β (IL-1β) specifically stimulates macrophages, while TNF-α (Tumor Necrosis Factor alpha) and Flt-3 ligand specifically stimulate dendritic cells. Heat killed *Mycobacterium butyricum* and Interleukin-6 (IL-6) are specific stimulators of B cells, and Interleukin-2 (IL-2) is a specific stimulator of T cells. Vector compositions comprising such component-specific immunostimulating agents provide for specific activation of macrophages, dendritic cells, B cells and T cells, respectively. For example, macrophages are activated when a vector composition comprising the component-specific immunostimulating agent IL-1β is administered. A preferred composition is IL-1β in association with colloidal metal, and a most preferred composition is IL-1β in association with colloidal metal and an antigen to provide a specific macrophage response to that antigen.

Vector compositions can further comprise targeting molecules, integrating molecules, PEGs or derivatized PEGs.

Many elements of the immune response may be necessary for an effective immune response to an antigen. An embodiment of a method of simultaneous stimulation is to administer four separate preparations of compositions of component-specific immunostimulating agents comprising 1) IL-1β for macrophages, 2) TNF-α and Flt-3 ligand for dendritic cells, 3) IL-6 for B cells, and 4) IL-2 for T cells. Each component-specific immunostimulating agent vector composition may be administered by any route known to those skilled in the art, and may use the same route or different routes, depending on the immune response desired.

In another embodiment of the methods and compositions of the present invention, the individual immune components are activated sequentially. For example, this sequential activation can be divided into two phases, a primer phase and an immunization phase. The primer phase comprises stimulating APCs, preferably macrophages and dendritic cells, while the immunization phase comprises stimulating lymphocytes, preferably B cells and T cells. Within each of the two phases, activation of the individual immune components may be simultaneous or sequential. For sequential activation, a preferred method of activation is administration of vector compositions that cause activation of macrophages followed by dendritic cells, followed by B cells, followed by T cells. A most preferred method is a combined sequential activation comprising the administration of vector compositions which cause simultaneous activation of the macrophages and dendritic cells, followed by the simultaneous activation of B cells and T cells. This is an example of methods and compositions of multiple component-specific immunostimulating agents to initiate several pathways of the immune system.

Figure 11:
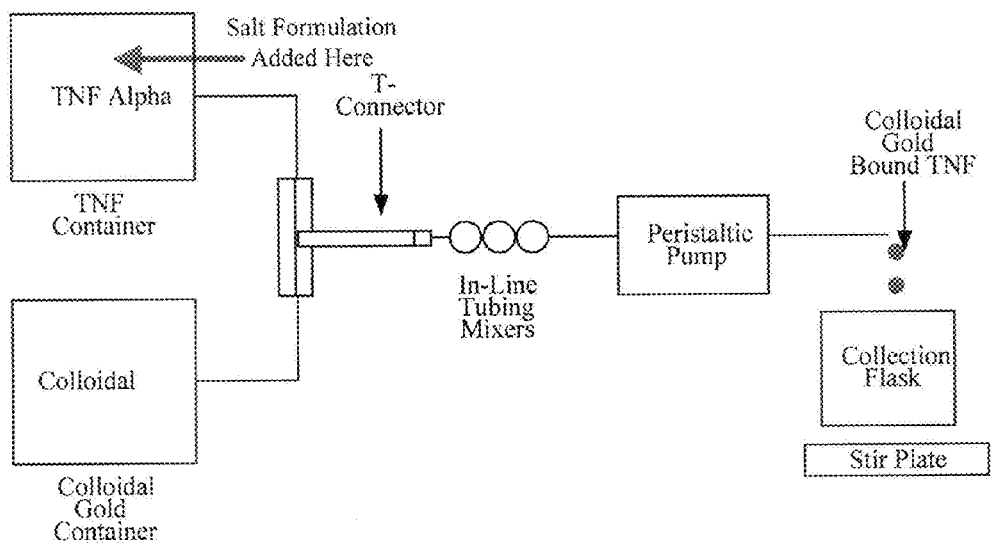
FIG. 11 provides a schematic representation of the colloidal gold/TNF binding apparatus FIG. 12 provides a graph of the effect of ionic strength on the stability of the colloidal gold TNF vector after lyophilization.
Figure 12:
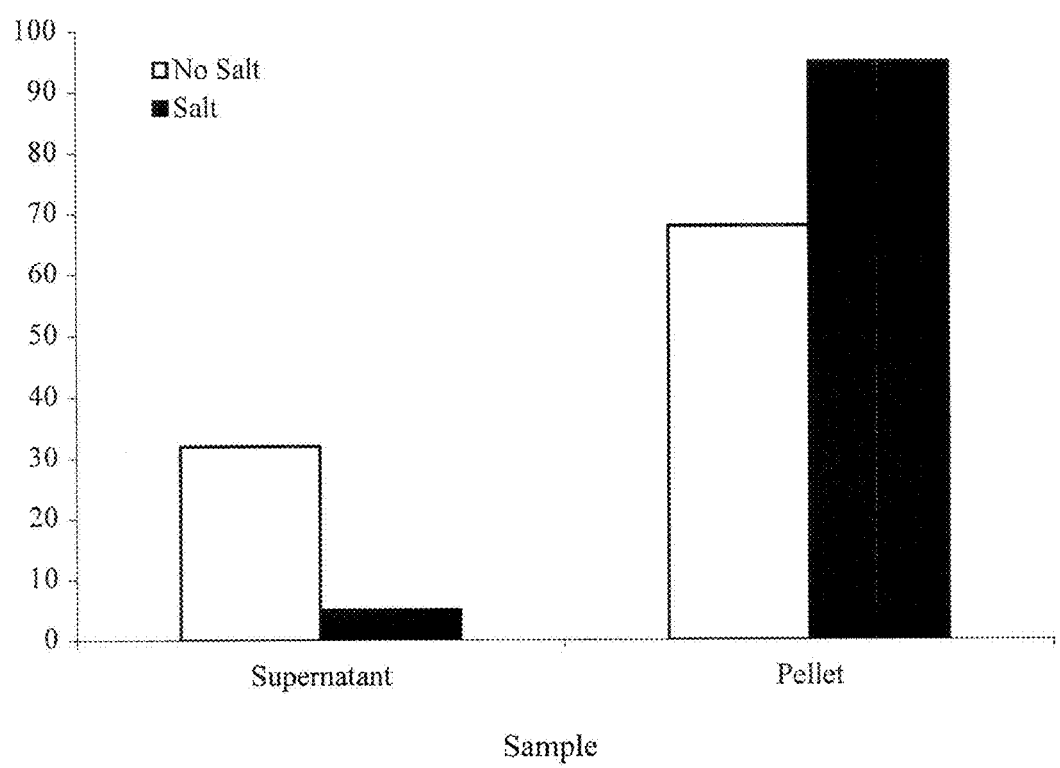
Figure 13:
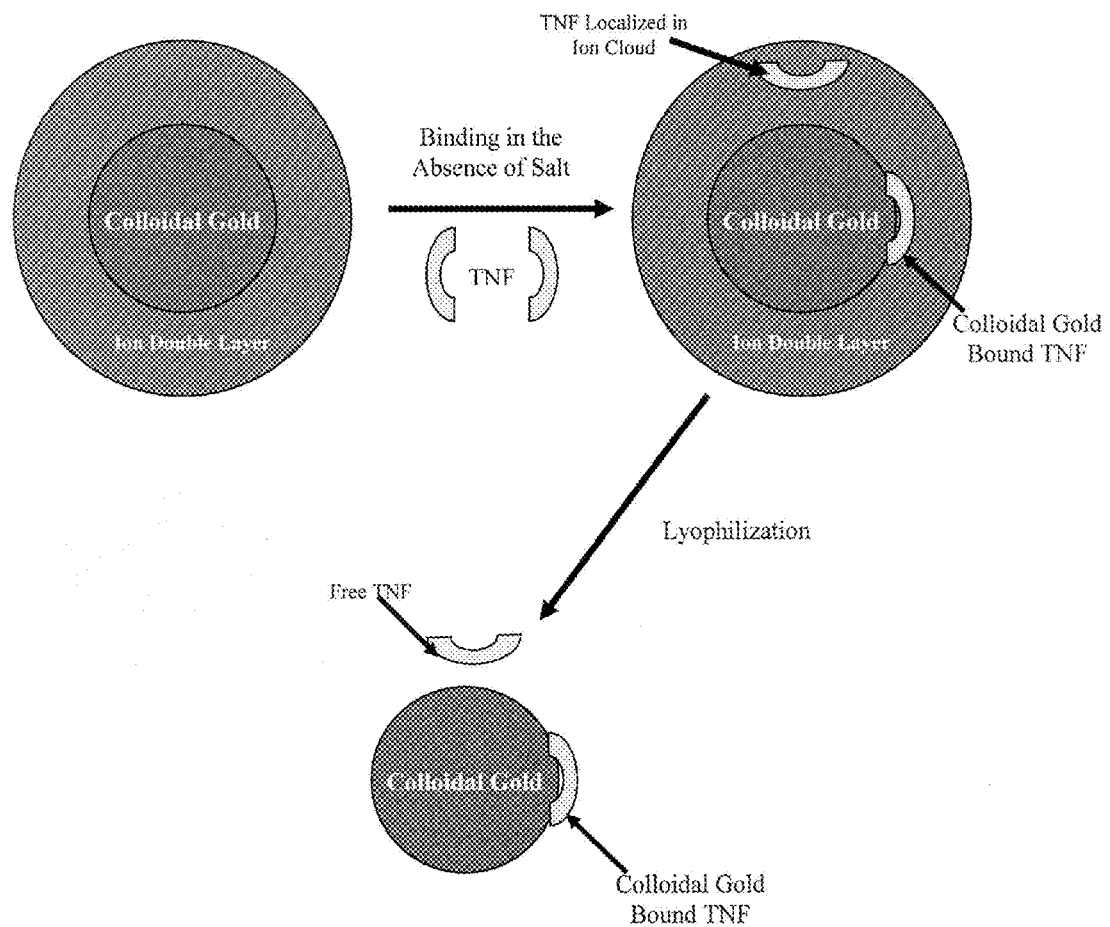
FIG. 13 provides a schematic representation of a model for TNF binding to colloidal gold in low ionic strength solutions.
Figure 14:
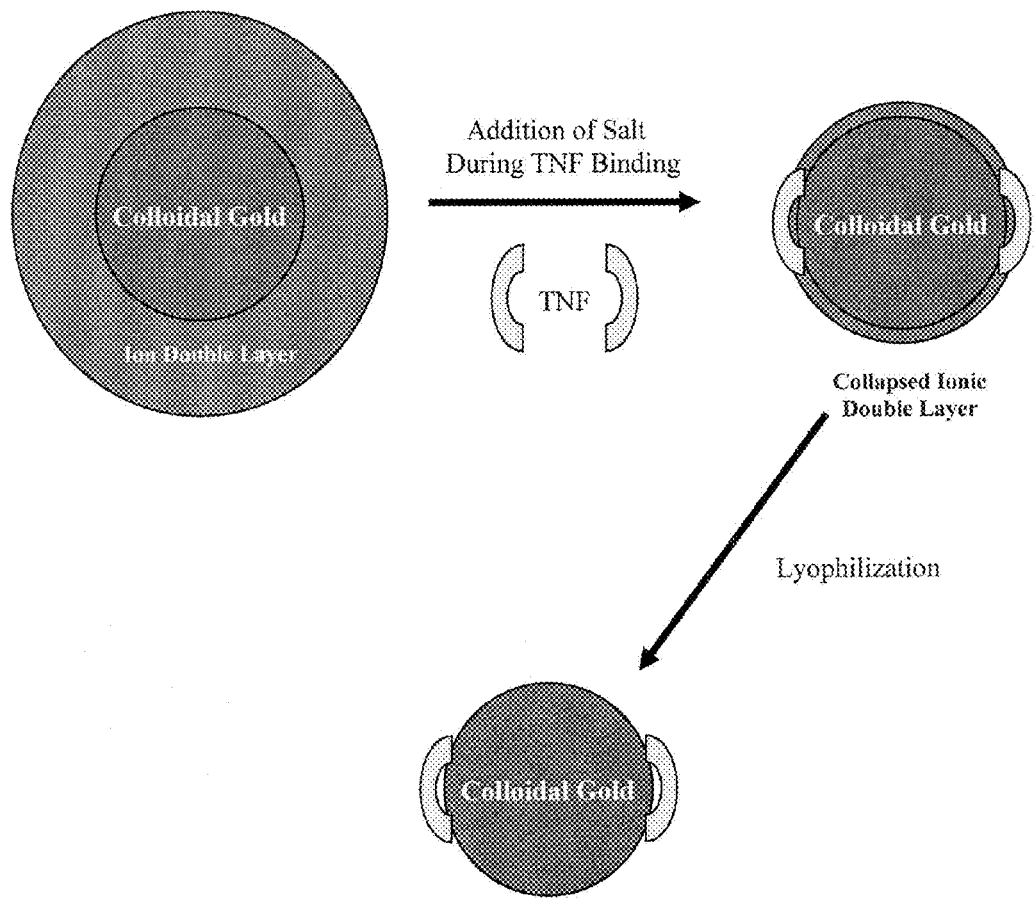
FIG. 14 provides a schematic representation of a model for TNF binding to colloidal gold at high ionic strength solutions.

One method of binding an agent to metal sols comprises the following steps, though for clarity purposes only, the methods disclosed refer to binding a single agent, TNF, to a metal sol, colloidal gold. An apparatus was used that allows interaction between the particles in the colloidal gold sol and TNF in a protein solution. A schematic representation of the apparatus is shown in FIG. 11. This apparatus maximizes the interaction of unbound colloidal gold particles with the protein to be bound, TNF, by reducing the mixing chamber to a small volume. This apparatus enables the interaction of large volumes of gold sols with large volumes of TNF to occur in the small volume of a T connector. In contrast, adding a small volume of protein to a large volume of colloidal gold particles is not a preferred method to ensure uniform protein binding to the gold particles. Nor is the opposite method of adding small volumes of colloidal gold to a large volume of protein. Physically, the colloidal gold particles and the protein, TNF are forced into a T-connector by a single peristaltic pump that draws the colloidal gold particles and the TNF protein from two large reservoirs. To further ensure proper mixing, an in-line mixer is placed immediately down stream of the T-connector. The mixer vigorously mixes the colloidal gold particles with TNF, both of which are flowing through the connector at a preferable flow rate of approximately 1 L/min.

Prior to mixing with the agent, the pH of the gold sol is adjusted to pH 8-9 using 1 N NaOH. A preferred method for adjusting the pH of the gold sol uses 100 mM TRIS to adjust the pH of the colloidal gold sol to pH 6. Highly purified, lyophilized recombinant human TNF is reconstituted. A preferred method for diluting TNF is in water that has been adjusted to pH 6 with 100 mM TRIS. Before adding either the sol or TNF to their respective reservoirs, the tubing connecting the containers to the T-connector is clamped shut. Equal volumes of colloidal gold sol and TNF solution are added to the appropriate reservoirs. Preferred concentrations of the active agent in solution range from approximately 0.01 to 15 μg/ml, and can be altered depending on the desired ratio of the agent to metal sol particles. Preferred concentrations of TNF in the solution range from 0.5 to 4 μg/ml and the most preferred concentration of TNF for the TNF-colloidal gold composition is 0.5 μg/ml.

Once the solutions are properly loaded into their respective reservoirs, the peristaltic pump is turned on, drawing the agent solution and the colloidal gold solution into the T-connector, through the in-line mixer, through the peristaltic pump and into a collection flask. The mixed solution is stirred in the collection flask for an additional hour of incubation.

In compositions comprising PEG, whether derivatized or not, the methods for making such compositions comprise the following steps, though for clarity purposes only, the methods disclosed refer to adding PEG thiol to a metal sol composition. Any PEG, derivatized PEG composition or any sized PEG compositions or compositions comprising several different PEGs, can be made using the following steps. Following the 15-minute incubation, a thiol derivatized polyethylene glycol (PEG) solution is added to the colloidal gold/TNF sol. The present invention contemplates use of any sized PEG with any derivative group, though preferred derivatized PEGs include mPEG-OPSS/2,000, mPEG-OPSS/5,000, mPEG-OPSS/10,000, mPEG-OPSS/12,000, mPEG-OPSS/20,000, mPEG-OP(SS)$_2$/2,000, mPEG-OP(SS)$_2$/3,400; mPEG-OP(SS)$_2$/8,000, mPEG-OP(SS)$_2$/10,000, thiol-PEG-thiol/2,000, mPEG-thiol 5,000, and mPEG thiol 10,000, mPEG thiol 12,000, mPEG thiol 20,000 (Sun-BIO Inc.). A preferred PEG is mPEG-thiol 5000 at a concentration of 150 μg/ml in water, pH 5-8. Thus, a 10% v/v of the PEG solution is added to the colloidal gold-TNF solution. The gold/TNF/PEG solution is incubated for an additional 15 minutes.

In a preferred method, the TNF and PEG-THIOL moiety simultaneously binds to the colloidal gold nanoparticle. In this method the pH of the colloidal gold nanoparticles is adjusted to 6.0 using 100 mM TRIS Base. Similarly the pH of water is adjusted to 6.0 using the 100 mM TRIS solution. Into the latter solution TNF and PEG-THIOL (20,000) are diluted to a final concentration of 5 and 15 ug/ml, respectively. Both the colloidal gold nanoparticles and TNF/PEG-THIOL solutions are loaded into their respective reservoirs and bound through the T-connector and in-line mixer using a peristaltic pump to draw each solution through the T-connector. After binding for 15 minutes Human Serum Albumin (200 μg/ml in $H_2O$) is added to the colloidal gold/TNF/PEG-THIOL solution and incubated for an additional 15 minutes.

The colloidal gold/TNF/PEG solution is subsequently ultrafiltered through a 50-100K MWCO diafiltration cartridge. The 50-100K retentate and permeate are measured for TNF concentration by ELISA to determine the amount of TNF bound to the gold particles.

After diafiltration, cryoprotectants, such as a compositions of mannitol, 20 mg/ml; and/or human serum albumin, 5 mg/ml, are added and the samples frozen at −80° C. The samples are lyophilized to dryness and sealed under a vacuum, subsequently reconstituted and analyzed for the amount of free and colloidal gold bound TNF present in the reconstituted samples.

The compositions of the present invention can be administered to in vitro and in vivo systems. In vivo administration may include direct application to the target cells or such routes of administration, including but not limited to formulations suitable for oral, rectal, transdermal, ophthalmic, (including intravitreal or intracameral) nasal, topical (including buccal and sublingual), vaginal or parenteral (including subcutaneous, intramuscular, intravenous, intradermal, intratracheal, and epidural) administration. A preferred method comprising administering, via oral or injection routes, an effective amount of a composition comprising vectors of the present invention.

The formulations may conveniently be presented in unit dosage form and may be prepared by conventional pharmaceutical techniques. Pharmaceutical formulation compositions are made by bringing into association the metal sol vectors and the pharmaceutical carrier(s) or excipient(s). In general, the formulations are prepared by uniformly and intimately bringing into association the compositions with liquid carriers or finely divided solid carriers or both, and then, if necessary, shaping the product.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Manufacture of Colloidal Gold

Colloidal gold sols are manufactured using the reaction described by Frens and Horisberger (Frens, G. Nature Phys. Sci. 1972, 241, 20-22, and Horsiberger, M. Biol. Cellulaire. 1979. 36: 253-258). In this reaction ionic gold, in the form of $HAuCl_4$, is reduced to nanoparticles of $Au^0$ by the addition of sodium citrate. Typically, 2.5 ml of a 4% chloroauric acid (in water) solution is added to 1 L of deionized water. The solution is vigorously stirred and heated to a rolling boil. The reduction reaction is initiated by the addition of a 1% sodium citrate solution. The size of the particle is controlled by the amount of citrate added to the reaction. For example, 17, 32, and 64 nm particles are formed by the addition of 40, 15, and 7.5 ml of the citrate solution, respectively. After the addition of citrate, the solution is allowed to boil and mix for an additional 45 minutes. Upon cooling, the sol is filtered through a 0.22 μm sterilization filter and stored at room temperature until used.

The production of colloidal gold sols has been scaled-up from 1.0 L to 10 L. UV-VIS wavelength scans, dynamic light scattering, and differential centrifugation techniques are used to check these particles for average particle size and homogeneity. Manufactured particles have a mean particle size that routinely measures within 10% of their predicted size and exhibit a poly-dispersity measure of 1.03-1.12 or less.

Example 2

Increasing the Number of Immune Competent B Cells

To increase the number of immune competent B cells for immunization, MHC class II restricted-surface $IgM^+/sIgD^+$ human B cells are isolated from units of whole blood or buffy coats. Magnetic beads coated with anti-IgM, anti-IgD and anti-CD19 antibodies separate the B cell populations. Treating $sIgM^+/sIgD^-$ immature B cells with the cytokine interleukin-7 is used to recruit additional B cells (Sudo, T., Ito, M., Ogawa, Y., Iizuka, M., Kodoma, H., Kunisasa, T., Hayashi, S. C., Ogawa, M., Sakai, K., Nishikawa, S., Nishkawa, S. C. J. Exp. Med. 1989. 170: 333-338). This treatment has been shown to mature these B cells as signaled by the phenotype conversion of $sIgM^+/sIgD^-$ B cells to $sIgM^+/sIgD^+$ B cells. These isolated cells are purified to near homogeneity using FACS separation.

Conjugating TNF to carriers such as KLH or thyroglobulin (see discussion below) enhances the antigenicity of human TNF. TNF:KLH antigen is bound to the surface of colloidal gold particles which contain a B cell targeting/activating agent such as interleukin-6 (IL-6). IL-6 is a cytokine known to stimulate the synthesis of antibodies from immunized B cells. Having both moieties on the same particle of gold, ensures that B cells receive the KLH:TNF antigen signal as well as the IL-6 signal to activate the antibody response.

Example 3

Differentiation of the Primary Antibody Response

Critical to the production of a therapeutic antibody is the process of class switching. The primary antibody response from immunized human B cells results in the secretion of IgM antibodies. A second class of lymphoid cells, known as antigen presenting cells (APCs), also internalizes the antigen. Once internalized these cells process the protein antigen into fragments, which are then expressed on the cell's surface bound to one of two major histocompatibility complexes (MHCs).

Depending on the microenvironment, APCs expressing antigen bound to class II MHC molecules activate one of two subsets of $CD4^+$ T cells. These cells, also known as helper T cells, perform the necessary accessory functions to facilitate the cellular or the humoral (antibody) immune response. $T_H1$ $CD4^+$ cells facilitate the cellular immune response, while the $T_H2$ subset of $CD4^+$ cells interact with IgM secreting B cells to initiate the process of class switching.

The activation of $CD4^+$ $T_H2$ T cells by the APC occurs with the formation of a bicellular cleft known as the immune synapse. The formation of the immune synapse involves interaction and rearrangement of signaling and structural ligands on the APC with their respective receptors on the T cell to form a three-dimensional (3-D) bridge that allows contact and signaling between these two cells (FIG. 1). Antigen signaling between the APC and the T cell occurs through the binding of the MHC/antigen complex with the T cell receptor complex, while the structural integrity of the immune synapse is maintained by the interaction of ICAM, LFA-3, and CD72 on the APC with LFA-1, CD2, and CD5 receptors on T cells, respectively. The successful formation of the immune synapse causes the $CD4^+$ T cell to express a B cell stimulatory molecule known as CD40 ligand.

The formation of the immune synapse may signal the T cell to become active or inactive (anergic). Which response is initiated is dependent on the strength of the co-stimulatory signals provided by the B7 molecule on the APC to the T cell. The B7 molecule may interact with either B7 receptor molecule on the T cell, CD28 or $CTLA_4$. These B7 receptors differ with respect to their density on the surface of the T cell as well as their affinity for the B7 molecule. CD28 has a lower affinity for B7 than $CTLA_4$, but is present at a much higher density on the surface of the T-cell. The binding of B7 to the CD28 receptor sends an activation signal to the T cell while the binding of B7 by $CTLA_4$ induces T cell anergy (Kuby, J., Immunology Third Edition 1997. eds Allen D., pp-213-218). Thus presenting excess B7 in the immune synapse will ensure that the T cells will be activated.

In this process immunized human B cells undergo rearrangement of the immunoglobulin genes to produce highly specific high affinity IgG antibodies.

This vector is initially assembled from MHC, B7, and ICAM proteins onto the surface of colloidal gold particles. The presentation of the immune synapse is in the 3-D orientation to allow this vector to successfully trigger CD4+T-cells to express CD40 ligand in an MHC-restricted fashion.

This process is also optionally initiated by using the sTc that expresses CD40 Ligand in combination with various cytokines and the synthetic germinal center whose multiple molecules signal the affinity maturation critical to a therapeutic mAb.

Example 4

Creation of sAPC/sTc/sGC with Spacer Arms

This sAPC is built on streptavidin colloidal gold particles that are used to bind biotinylated forms of the MHC, B7, and ICAM proteins. This single particle sAPC has a greater degree of flexibility, since the constituent proteins are bound to the colloidal gold particle indirectly through biotinylated spacer arms that form a biotin-avidin bridge. Similarly, the sTc and sGCs may be generated using a similar strategy for tethering their respective components to the colloidal metal.

Example 5

Self-Assembling APCs/sTcs/sGCs

Figure 5:
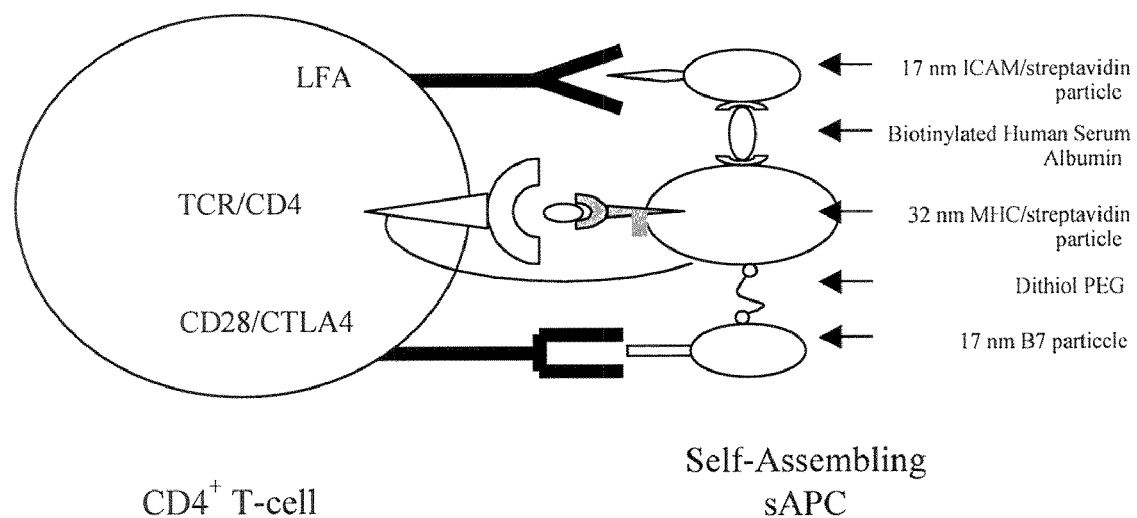
FIG. 5 provides a schematic representation of the generation of a multiple particle colloidal gold sAPC.

Self-assembling synthetic APCs are developed. Binding each APC protein to a different colloidal gold particle creates a complex matrix of immune synapse proteins. To direct the assembly of this sAPC, site directed molecular scaffolds are made to better orient the various particles in 3-D. Shown in FIG. 5 is a representation of this self-assembling sAPC. The formulation of each particle subunit allows for a single particle to bind multiple reagents. For illustration purposes the MHC class II molecule is bound to a 32 nm colloidal gold particle that is also bound with streptavidin. The remaining two subunits of the sAPC, the B7 and ICAM, are bound to 17 nm particles. Like the MHC particle the ICAM subunit contains streptavidin-docking sites. To assemble this particle biotinylated human serum albumin is used to join the ICAM and MHC particles together. To complete the assembly of the vector, dithiolated polyethylene glycol is used to link the MHC and B7 particles together.

In this model, the formation of the immune synapse occurs through T-cell receptor/membrane rearrangements. This vector may also be bound to a solid support stage such as an EIA plate. These scaffolds allow both colloidal gold-targeted antigens and sAPCs present in the same matrix. As a result, upon immunization of the naïve B-cell the sAPC may activate the CD4 cell to express CD40 ligand and as a result induce class switching.

By changing the binding partner to CD40L/cytokine or BLYS/CD30L the self-assembling synthetic T cells or synthetic germinal centers are generated.

Example 6

Binding of Proteins to Colloidal Gold Particles

The binding of proteins to colloidal gold particles is influenced by the pH of the colloidal gold sol and protein solutions. At an optimal pH, proteins bind to the surface of colloidal gold particles and prevent their precipitation by salts. Salt-induced precipitation of the colloidal gold is easily documented by the changes in the color of the sol from red to black. The pH binding optimum is determined for each protein described, including the MHC, B7, ICAM, IL-6 and the KLH:TNF antigen. As an example, the procedure described below outlines the method for binding the MHC molecule to the colloidal gold particles. A similar procedure will be used to determine the binding conditions for each of the other proteins The pH binding optimum for MHC binding to colloidal gold is determined by adjusting the pH of 1 ml aliquots of colloidal gold from 4-11 with 1N NaOH. 100 µl aliquots from each of the gold solutions are placed into micro-centrifuge tubes and incubated for 30 minutes with 1 ng of the MHC protein. 100 µl of a 10% NaCl solution is then added to each tube. The pH binding optimum is defined as the pH that allows the MHC protein to bind to the colloidal gold particles, while preventing salt-induced precipitation.

In addition to determining the pH binding optimum, a saturation binding analysis is performed for each protein. For this test the pH of the colloidal gold particles will be adjusted to the pH binding optimum as described above. Subsequently increasing amounts (0.025-5 ng of protein) of the MHC protein is added to the 100 µl aliquots of colloidal gold. After binding for 30 minutes, the various aliquots are centrifuged at 10,000 rpms to separate free from colloidal gold bound protein. The supernatant and colloidal gold pellets are analyzed for the relative amount of MHC protein present in each fraction.

Example 7

Quantification of the Mass of the MHC Protein Bound

To quantify the mass of the MHC protein bound per particle of gold, quantitative EIAs are developed for the measurement of the MHC and B7 proteins. EIAs for ICAM are already commercially available. The MHC and B7 proteins are quantitatively measured by developing a competitive binding EIA for each protein. Commercially available antibodies to B7 and MHC proteins (both antibodies are available from Research Diagnostics, Inc.) are coated onto EIA plates using a carbonate/bicarbonate buffer at pH 9.6. MHC and B7 reference standards are generated to provide a dose range of 1.56 ng/ml to 500 ng/ml. These standards are added to the EIA plate containing specific antibodies for either the MHC or B7 protein. The colloidal gold bound samples are added to other designated wells in the EIA plate.

The concentration of the various proteins is determined by establishing a competitive binding reaction between the protein present in the sample or standard and a biotinylated form of the molecule for antibody sites. The biotinylated ligand is detected with streptavidin alkaline phosphatase. Upon the addition of substrate, an inverse relationship is generated between the mass of analyte present in the sample and the amount of color developed.

Example 8

Binding Multiple Proteins to the Same Particle

To increase the efficiency and specificity of the in vitro immunization multiple chemically distinct proteins need to be bound onto the surface of a single colloidal gold particle. The binding of three different protein cytokines (IL-1, IL-6 and TNF) to the same particle of colloidal gold is demonstrated. Each cytokine binds to colloidal gold at a specific pH.

As demonstrated above, it was determined that IL-1 bound to colloidal gold at a pH between 6 and 8 while TNF and IL-6 bound at a pH of 8 and 11, respectively. A solution containing 0.25 ng/ml of the three cytokines in water was mixed with a colloidal gold sol at pH 8. A sample was removed and the pH of the remaining solution was adjusted to 11. Prior to each pH change additional samples were collected. The two samples were centrifuged and the resultant pellets of colloidal gold were re-suspended in PBS.

Figure 6:
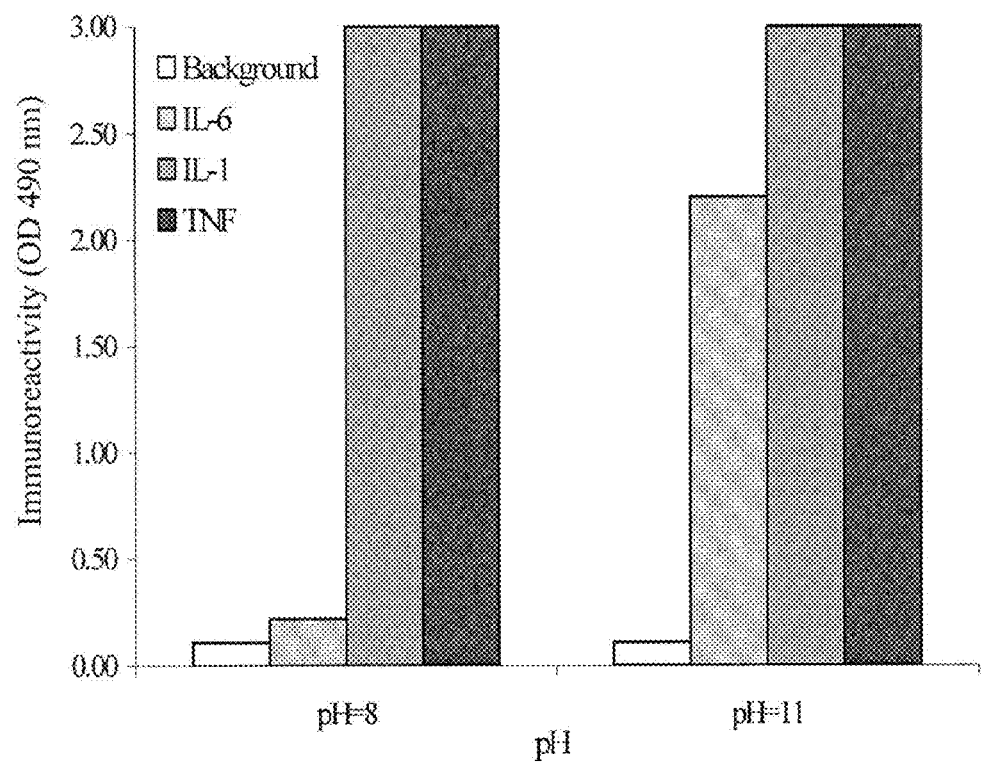
FIG. 6 provides a graph depicting the binding multiple cytokines to the same particle of colloidal gold.
Figure 7:
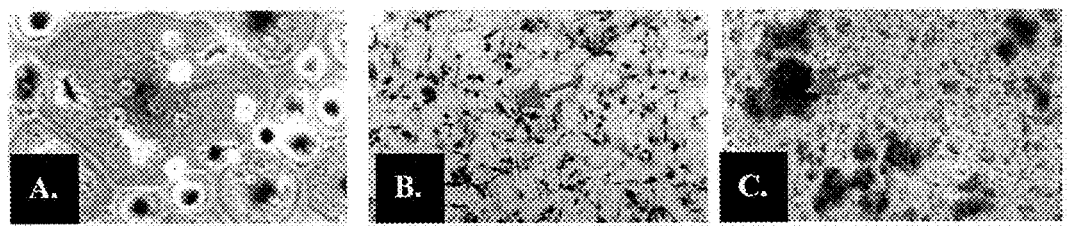
FIG. 7 is a series of photographs of EGF streptavidin gold that was targeted to macrophages (FIG. 7A), dendritic cells (FIG. 7B) and B-Cells (FIG. 7C).
Figure 8:
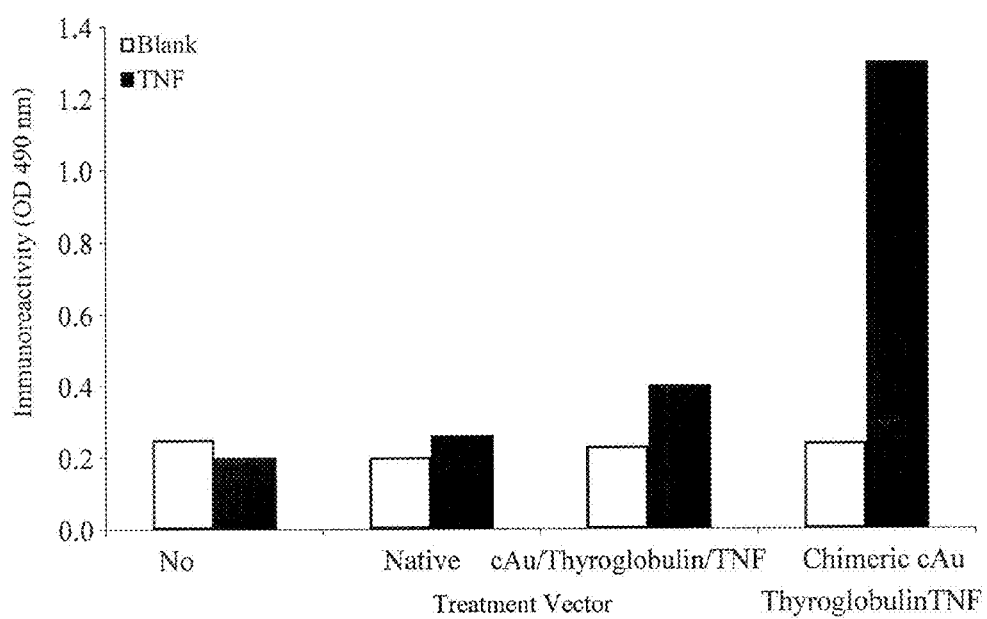
FIG. 8 provides a graph of the immunoreactivity of cells in response to various stimuli in vitro.

To demonstrate the presence of all three cytokines on the same particle of gold the various pellets were added to an EIA plate that was coated with a monoclonal antibody to TNF. After binding, the plate was washed and designated wells were incubated with either an alkaline phosphatase conjugated rabbit anti IL-1, IL-6, or TNF. After a wash, substrate was added to each well to initiate color development. The data presented in FIG. 6 show that due to the overlap in pH binding optimum both IL-1 and TNF were present on the particle at pH 8. However, very little IL-6 signal could be detected. Increasing the pH 11 allowed IL-6 to bind to these particles.

Example 9

Targeting of Chimeric Vectors to Specific Cells

EGF and streptavidin were bound to the same 32 nm particle of colloidal gold. The sample was divided into three aliquots for the binding of secondary/targeting molecules. One sample was bound with biotinylated IL-1, another biotinylated GM-CSF, and the third with biotinylated IL-6. After binding the biotinylated ligands, the samples were centrifuged to remove any free reagents and the colloidal gold pellets were added to Ficoll-separated human white blood cells. After 8 days in culture the uptake of the various colloidal gold vectors was documented by digital photography.

EGF streptavidin gold was targeted to macrophages (FIG. 7A), dendritic cells (FIG. 7B) and B-Cells (FIG. 7C) by using biotinylated IL-1, biotinylated GM-CSF, or biotinylated IL-6 for targeting. The black staining (highlighted by the red arrows) in each of the figures represents the uptake of the various colloidal gold vectors.

As can be seen in FIG. 7, the various colloidal gold/cytokine chimeras differentially targeted the various cellular elements of the immune system. The black staining (highlighted by the arrows) represents the colloidal gold particles, which have been internalized and aggregated by the various immune cells. These data indicate that IL-1 targeted the colloidal gold EGF to macrophages, while GM-CSF targeted the chimera to dendritic cells, and IL-6 targeted the vector to B cells.

Example 10

Immunization of Human Lymphocytes

These vectors can be used to generate a primary immune response from isolated lymphocytes. White blood cells were collected from whole blood by density centrifugation. These cells were treated with a thyroglobulin conjugated TNF/IL-6 colloidal gold vector. The cells received pulses of the colloidal gold vector every 2 days for a total of eight days. After the final pulse, the cells were cultured for another 5 days. The supernatants were collected and tested for the presence of human anti-human TNF (IgM/IgD and IgG combination) antibodies using a direct EIA. As can be seen in FIG. 8, the chimeric cAU thyroglobulin TNF had the highest immunodensity.

Example 11

Immunization of Human B-Cells and Dendritic Cells for Class II MHC Expression

Two different approaches to increase the efficiency of in vitro human lymphocyte immunization are used. First, coupling TNF to immunogenic carriers, such as Thyroglobulin, Keyhole Limpet Hemocyanin or Murine Serum Albumin enhances TNF's immunogenicity. Carrier:TNF conjugations are performed using standard EDC/NHS and gluteraldehyde methods. Second, coupling them to particles of colloidal gold, containing cell-specific targeting agents increases the specificity of these antigens. To target the delivery of the antigen to B cells the carrier:antigen complex is bound to particles of colloidal gold particles containing IL-6. To target the delivery of the carrier antigen to dendritic cells the carrier: antigen complex is bound to colloidal gold particles containing GM-CSF.

These vectors are initially used to immunize naïve MHC restricted human B cells and dendritic cells for the generation of the class II MHC antigen.

These same vectors are used at a later time to induce the primary antibody response from a new or replicate set of naïve B cells. The immunization scheme involves the sequential immunization of B cells and dendritic cells with the various vectors. As a result the B cells and dendritic cells see the carrier once and the TNF antigen three times.

Example 12

Generation of Class II MHC Protein by B Cells

To cause human B-cells to produce class II MHC protein, $10^6$ surface $IgM^+/IgD^+$ human B-cells are plated in 24-well plates and cultured in 1.5 ml of AIM V media. Twenty four hours after plating, the cells are pulsed with the THYRO:TNF antigen bound to an IL-6 targeted colloidal gold vector. Two days later the cells are pulsed with the KLH:TNF carrier targeted by the IL-6 vector. After an additional two days in culture the cells are immunized with the third carrier:TNF antigen, MSA:TNF. The cells are incubated for an additional three to seven days and tested for the presence of Class II MHC expression by FACS analysis. Alternatively, the cells may be simultaneously pulsed with the colloidal gold antigens.

A similar procedure is used to pulse dendritic cells to express the MHC class II protein. These cells are immunized with the TNF:carrier antigen bound to GM-CSF targeted colloidal gold vectors. Dendritic cell precursors are isolated from peripheral blood using magnetic beads coated with anti-CD34. These cells are expanded in vitro by incubating them in AIM V serum free media supplemented with 1000 ng/ml of GM-CSF and 100 ng/ml of IL-4. Upon their maturation, confirmed by FACS analysis for the detection of CD1a and empty class II MHC molecules, the cells are differentiated into mature dendritic cell with a 10 ng/ml pulse of TNF. These mature dendritic cells are immunized with the GM-CSF targeted colloidal gold TNF antigen. Antigen loaded MHC class II protein complexes are detected by FACS or in situ analysis of the biotinylated antigen peptide detected with a streptavidin conjugated phycoerythrin (Research Diagnostic Inc.) detection system.

Example 13

Method Development for the Isolation of the MHC Class II Antigen

The method for the isolation of the MHC uses "generic"-non-MHC compatible blood samples. These MHC molecules are used to define the pH and saturation optima for the protein on colloidal gold particles. Once defined, these methods are adapted to purify antigen loaded MHC from immunized MHC restricted blood pools.

The isolation of generic and antigen loaded human class II MHC is done using the method described by Sette (Sette et al., J. Immunol. 1992. 148: 844). Briefly the buffy coats from non-HLA matched human whole blood are frozen at a minimum density of $10^8$ cells/ml and sonicated to disrupt the cells. These cells are suspended in a buffer of 50 mM TRIS-HCl, pH 8.5 with 2% Renex, 150 mM NaCl, 5 mM EDTA and 2 mM PMSF. Large particulates including the nuclei are removed by centrifugation (10000×g for 20 minutes). The cell lysate is then fractionated on an affinity column made by binding murine antibodies to the human class II MHC molecule (Research Diagnostics Inc.) to protein A/G sepharose beads. The lysate is passed through the column at least 5 times to maximize the binding of the MHC protein to the immobilized antibody. The column is washed with 10 column volumes of a buffer containing 10 mM TRIS-HCl pH 8.0/0.1% Renex followed by an additional wash of 5 column volumes of PBS with 1% n-ocytlglucoside. The MHC class II protein is eluted from the column using a buffer of 50 mM diethylamine in saline with 1% n-ocytlglucoside at a pH 11.5. Upon elution each fraction is immediately neutralized with the addition of 2 M glycine, pH 2.0. The fractions containing the MHC II molecules are aliquoted and lyophilized in 25 µg aliquots.

Example 14

Generation of Human B7.1 Molecule

The human co-stimulatory molecule B7.1 is made by recombinant DNA technology. The gene is supplied as part of a commercially available transient expression vector system (InVivogen Inc.). The construct is provided with the appropriate restriction sites allowing for the separation of the active gene from the plasmid construct. The human B-7.1 gene is isolated from the pORF host plasmid using the restriction enzyme NcoI and NheI. This double digestion results in the formation of two linearized pieces of DNA. One of the gene fragments consists of the B-7.1 gene (893 bp) while the other fragment (3210 bp) constitutes the accessory genes of the p-ORF plasmid. The gene fragments are fractionated on a 1% agarose gel and visualized by ethidium bromide staining. The bands are cut from the gel and purified using QuiaQuick gel extraction resin. The purified linearized gene is inserted into a baculovirus expression system (CloneTech Inc.) under the control of the strong CMV promoter. The baculovirus incorporated genes are transfected into the SF9 insect cell line according to the manufacturers specifications and conditions. $10^6$ B7 transfected NOS cells will be expanded in bioreactors. The incubation media and cell lysates are processed by affinity chromatography using a murine monoclonal antibody against the human B7.1 protein (Research Diagnostics Inc.) previously immobilized to a protein A/G sepharose column.

Example 15

Generation of the Synthetic Antigen Presenting Cell

The Single Particle sAPC

To mature the primary antibody response the sAPC capable must induce the CD4 T-cell/B-cell interactions that result in antibody class switching. The first sAPC is developed by binding the proteins of the immune synapse on a single particle of colloidal gold. This vector as well as one built on a streptavidn colloidal gold core are tested for their ability to activate $CD4^+$ T-cells.

Once the components of the immune synapse are isolated and purified to homogeneity they are bound to colloidal gold particles to develop the single particle sAPC. Two strategies are used to develop these APCs. The first strategy involves the direct binding of the components of the immune synapse (i.e., the peptide loaded MHC, B7 and ICAM molecules) to particles of colloidal gold. While not wishing to be bound, it is believed that each ml of gold will bind 250 ng of each protein/ml of colloidal gold sol.

Figure 9:
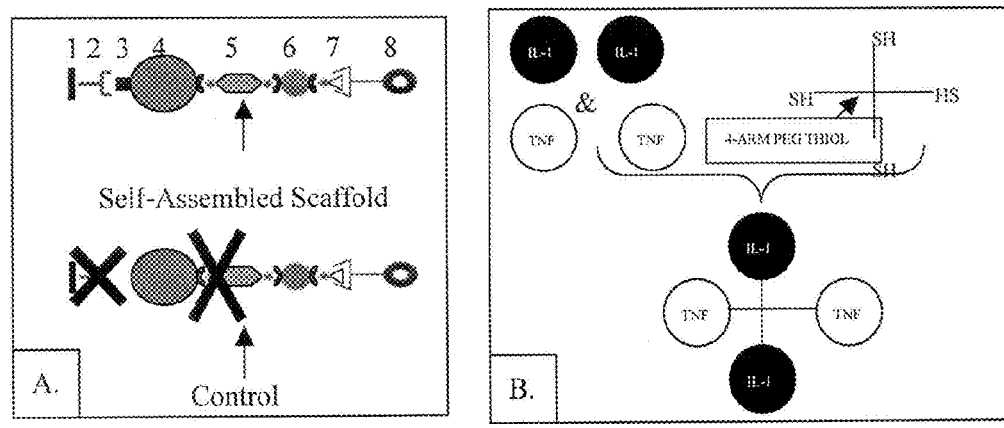
FIG. 9A provides a schematic of the self-assembly of colloidal gold particle on the solid support of an EIA plate. 1=EIA plate; 2=Murine Mab against human TNF; 3=human TNF (blue box); 4=32 nm colloidal gold bound with streptavidin an TNF; 5=biotinylated BSA; 6=17 nm streptavidin colloidal gold; 7=biotinylated human IL-6; 8=alkaline phosphatase conjugated rabbit anti-human IL-6.
FIG. 9B provides a schematic of self-assembly of colloidal gold particles bound with either IL-1 or TNF on a four-arm PEG-thiol backbone (Sun Bio, Inc.).
Figure 10:
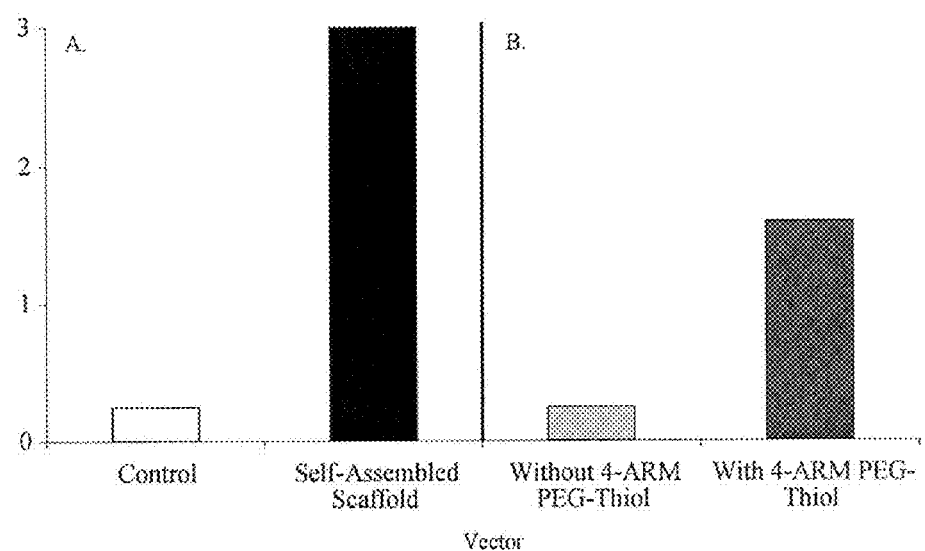
FIG. 10A provides a graph of the immunoreactivity signal generated by the particle in FIG. 9A.
FIG. 10B provides a graph of the immunoreactivity signal generated by the particle in FIG. 9B.

The first scaffold was assembled on the surface of an EIA plate. The materials include an EIA plate coated with a monoclonal antibody to human TNF; a 32 nm TNF/streptavidin colloidal gold chimera; biotinylated BSA: a 17 nm streptavidin colloidal gold vector; biotinylated human IL-6, Rabbit anti human IL-6 conjugated to alkaline phosphatase. The various components were assembled into a scaffold as depicted in FIG. 9A. The control for this study simply was the 32 nm particle without the TNF docking site upon which the scaffold was built. As presented in FIG. 10A a strong signal was generated when all of the molecular bricks of the scaffold were present. By merely omitting the TNF docking site the scaffold did not form and as a result no signal was generated.

The direct binding of the immune synapse proteins to a single particle of colloidal gold results in a rigid orientation of the proteins on the surface of the particle. To increase the flexibility of movement for these proteins on sAPC an alternative single particle sAPC is developed. This single particle sAPC is developed on a streptavidin colloidal gold platform that binds biotinylated forms of the MHC, B7, and ICAM proteins. The proteins are bound to the streptavidin gold particle through the biotin residue that is linked to the protein through a spacer arm.

The proteins are biotinylated using several biotinylating reagents such as NHS-Biotin (Pierce Chemical Co.). This reagent places a 1.35 nm spacer arm between the protein and biotin moieties. Alternatively, NHS-LC-LC-Biotin is used to biotinylate the proteins. This agents place a 3.05 nm spacer arm between the protein and biotin residue. Such a spacer arm facilitates movement of the proteins to promote ligand binding. This added flexibility improves the ability of the proteins to achieve a proper 3-D orientation and to form a functional immune synapse with the $CD4^+$T-cell.

Example 16

Generation of a Self-Assembling sAPC

The multiparticle sAPC will have the flexibility of self orientation during immune synapse formation. The flexibility is a direct result of assembling the moieties used to join the particles together. Linkers can be alkane, protein, and polyethylene glycol (PEG) to allow for the greatest vector functionality.

The second scaffold (shown in FIG. 9B) was assembled using a four-arm Polyethylene glycol (10,000 MW) backbone containing four terminal free thiols. This linker was used to join individual particles of colloidal gold bound with either IL-1 or TNF. After linkage the preparation was centrifuged and assayed for both proteins using an EIA plate coated only with an IL-1 monoclonal antibody. After binding the plate was washed and detected using enzyme linked IL-1 or TNF polyclonal antibodies. Similarly the vector described in FIG.

9B generated a signal (FIG. 10 B) for both proteins only in the presence of the linker. Without the linker only background color was observed.

To further increase the flexibility of the sAPC the component proteins are assembled on different particles of colloidal gold. These particles are assembled into a scaffolding system to generate a sAPC capable of inducing $CD4^+$ T-cell activation. The multi-particle sAPC may be used in solution or as is shown in FIGS. 9A and 9B to provide a solid support on an EIA plate.

The MHC, B7 and ICAM proteins are bound to different particles of colloidal gold as previously described. The particles are physically joined by a variety of scaffolding molecules. The function of the "joining" molecules is to provide greater flexibility of the individual particles of colloidal gold in the formation of the immune synapse. This flexibility occurs whether the sAPC is provided as an independent particle or as part of a matrix bound to a solid surface.

The first additive consists of modified di-thiol alkane moieties. The function of alkane di-thiol binds, through the formation of a thiol-gold bond, the individual particles of colloidal gold together. These moieties have been used to build self-assembling gold structures on the surface of glass slides in the development of biosensors (Mirkin, C. A., Letsinger, R., Mucic, R. C., and Storhoff, J. J. Nature. 1996. 382 607-609). The thiol group allows the binding of the alkane moiety directly to the surface of the colloidal gold particle. Examples of the commercially available alkane thiol reagents include: 1,5 pentane di-thiol, 1,6 hexane di-thiol, and decane di-thiol (Sigma Chemical Company).

As an alternative to the alkane di-thiols various sizes of 2, 3 and 4-arm poly-ethylene glycol (SunBio, Walnut Creek, Calif.) are also used. Each arm of these polymers has a free thiol group, which is used to bind the individual particles of colloidal gold through the formation of a gold-thiol bound. These reagents provide the added advantage of complete solubility in water.

Binding multiple protein moieties of the immune synapse to either single or multiple particles of colloidal gold enables the generation of a synthetic antigen-presenting cell (sAPC) capable of driving the cellular events that cause class switching in immunize human B-cells.

Example 17

Stimulation of $CD4^+$T-cells by sAPC to Express $CD4^+$ Ligand

Single particles and self-assembling sAPCs are tested for their ability to induce the expression of CD40 ligand from MHC restricted $CD4^+$ T-cells. Subsequently, 0.1 to 10 ug of antigen loaded MHC (present on the sAPC) are added to $10^6$ class II restricted $CD4^+$ T cells growing in AIM V media. The stimulation occurs in the presence of IL-4 and IL-10, which drives the production of the $T_H2$ subset of $CD4^+$ T cells. After 4, 12 and 24 hours of sAPC stimulation the CD4 cells are collected and stained with a FITC labeled mouse anti human CD40 ligand antibody and analyzed by FACS.

During the activation of the $CD4^+$ T cells a new set (i.e., cells not used for the isolation of the MHC) of MHC restricted B cell lymphocytes are immunized as was previously described to undergo the production of antigen specific IgM antibodies. MHC restricted B cells are immunized using the targeted TNF antigens previously described. Upon the detection of antigen specific IgMs and CD40 ligand production from their respective cells the activate $CD4^+$ T cells are added to IgM secreting B cells. Class switching is monitored by the detection human-anti-human TNF IgGs. IgG positive clones are fused with the K6H6/B5 mouse human heteromyeloma cell line as described below.

Example 18

Antibody Detection and Immortalization of B Cells

All of the cells from positive wells are combined, centrifuged once, washed with PBS and combined with $2\times10^6$ mouse/human heteromyeloma K6H6/B5 cells. The heteromyeloma cell line, K6H6/B5 (available through the ATCC), is an ideal fusion partner for these human lymphocytes because these cancer cells are non-secretors of antibody and are available with no patent restrictions. The human and myeloma cells are fused using standard fusion protocols with PEG. Successfully fused cells are selected using traditional HAT/HT selection protocols. A direct ELISA is used to test growing clones for the production of TNF specific human IgG antibody. Those clones that show antigen recognition are scaled-up in T-75 flasks, at which point all clones are cryopreserved and their supernatants tested for neutralizing antibody activity as described below.

Example 19

Neutralization of TNF Biologic Activity

The ability of the TNF antibodies to neutralize the biologic activity of TNF is tested using the well-characterized WEHI 164 bioassay. Briefly, TNF dose-dependently inhibits the in vitro proliferation of these cells.

For this bioassay 5000 WEHI cells are plated in 24-well tissue culture clusters. TNF (15.6 pg/ml to 500 pg/ml) is added to designated wells in the plate. To determine the ability of the human monoclonal antibodies to neutralize the action of TNF an identical standard dose range of TNF standards is made in the presence of 1 μg of each of the TNF monoclonal antibodies. The cells with the various treatments are cultured for 5 days and cell number is determined using a Coulter Counter.

Example 20

Effect of Ionic Strength on the Lyophilization Stability of Colloidal Gold Bound TNF The colloidal gold binding apparatus, shown in FIG. 11, was used to bind TNF to colloidal gold nanoparticles as previously described. After binding, 30K PEG-Thiol was added to the solution at 50 μg/ml in deionized water, pH 9.

To test the effect of ionic strength on the stability of the TNF-colloidal gold bond various amounts of salt (in the form of 1× normal phosphate buffered saline; PBS) were added to the container holding the TNF solution. Final concentrations of PBS varied from 0 to 0.325% of normal PBS. After binding and diafiltration, cryoprotectants (mannitol, 20 mg/ml; human serum albumin, 5 mg/ml) were added to the samples. The samples were subsequently aliquoted into 1 ml samples and frozen at ±80° C. After freezing the samples were lyophilized to dryness and sealed under a vacuum.

Subsequently the samples were reconstituted with 1 ml of deionized water and diluted ten-fold in a 1% PEG-1450/water solution. The samples were centrifuged to separate colloidal gold bound TNF from free TNF. Both the colloidal gold pellets and supernatants were analyzed for TNF concentrations by EIA. The data from these studies are presented in Table I.

TABLE 1

| Release Profile of Lyophilized Colloidal Gold TNF Manufactured in the Absence of Salt | |
|---|---|
| | Percent of Total TNF |
| Colloidal Gold Pellet | 68 |
| Supernatant | 32 |

Table I shows that 32% of the TNF is released from the vector following lyophilization. In repetitive studies we observed that as much as 50% of the protein is released after lyophilization.

Example 21

Effect of Increasing Ionic Strength on the Stability of a Lyophilized Colloidal Gold-TNF Drug The solution of TNF, which was previously diluted in a 3 mM TRIS solution to a final concentration of TNF of 0.5 μg/ml, was modified by adding 0.25× solution (77.25 milli-osmol/kg) of normal phosphate buffered saline. The solution was bound as was described above. After binding, 30K PEG-Thiol and the cryoprotectants described above were added and the samples frozen at −80° C. The samples were lyophilized as described above, subsequently reconstituted and analyzed for the amount of free and colloidal gold bound TNF present in the reconstituted samples. The data from this study are presented in FIG. 12.

As can be seen in FIG. 2, increasing the ionic strength significantly improves the stability of the vector during lyophilization. The salting effect was dose dependent. As shown in Table II as the amount of salt added to the TNF is decreased more of the protein is released after lyophilization.

TABLE II

| Effect of Salt Concentration on TNF Release Following Vector Lyophilization | | | | | |
|---|---|---|---|---|---|
| | Salt Concentration (milli-osmol/kg) | | | | |
| | 0 | 4.5 | 19.3 | 46.5 | 77.25 |
| Percent Released | 40 | 30 | 10 | 6 | 6 |

Binding TNF in the absence of salt results in a portion of the TNF being bound in the ionic double layer rather than directly on the gold particle (FIG. 13). During lyophilization water solvating the ionic layer is lost and thus upon reconstitution this vector released the portion of TNF bound in the ion cloud. By increasing the ionic strength through the addition of salt the ionic layer shrinks/collapses (FIG. 14) and allows for all of the TNF to bind directly to the particles' surface. After lyophilization, this preparation has all of the TNF bound to the particles' surface.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

What is claimed is:

1. A composition, comprising a synthetic antigen presenting cell (APC), wherein the synthetic APC comprises a major histocompatibility complex (MHC) protein bound to a first colloidal metal particle, a structural protein bound to a second colloidal metal particle, and a co-stimulatory protein B7 bound to a third colloidal metal particle, wherein the first, second and third colloidal metal particles are bound to each other by scaffolding molecules.

2. The composition of claim 1, wherein the MHC protein, the structural protein and the co-stimulatory protein B7 are bound indirectly by a binding pair.

3. The composition of claim 2, wherein the binding pair comprises streptavidin-biotin.

4. The composition of claim 1, wherein the structural protein is selected from the group consisting of: intracellular adhesion molecule (ICAM), LFA-3, and CD72.

5. The composition of claim 1, wherein the colloidal metal comprises colloidal gold, colloidal silver, colloidal iron, colloidal aluminum, or colloidal platinum.

6. The composition of claim 1, further comprising a pharmaceutically-acceptable component comprising excipients, buffers or carriers.

7. The composition of claim 1, further comprising an adjuvant, wherein the adjuvant comprises liposomes, emulsions, microspheres, biodegradable polymers and polystyrene, alum, heat killed *M. butyricum* and *M. tuberculosis*, Pertussis toxin and Tetanus toxin, or LPS and Staphylococcal enterotoxin B.

8. The composition of claim 1, wherein the MHC protein is an antigen-loaded MHC protein.

9. The composition of claim 1 wherein the colloidal metal particles are the same size.

10. The composition of claim 1, wherein the colloidal metal particles are different sizes.

11. The composition of claim 10, wherein the first colloidal metal particle is 32 nanometers (nm), and the second and third colloidal metal particles are 17 nm.

12. The composition of claim 1, wherein the first, second and third colloidal metal particles are coated with streptavidin and wherein the scaffolding molecule is a biotinylated protein.

13. The composition of claim 12, wherein the biotinylated protein is human serum albumin (HSA).

14. The composition of claim 1, wherein the scaffolding molecule is a di-thiol alkane.

15. The composition of claim 1, wherein the scaffolding molecule is a 2 or 4-arm poly-ethylene glycol (PEG).

* * * * *